(12) United States Patent
Robert et al.

(10) Patent No.: US 11,551,128 B2
(45) Date of Patent: Jan. 10, 2023

(54) BRANCHED HETEROPOLYMER LATTICE MODEL FOR QUANTUM OPTIMIZATION

(71) Applicant: International Business Machines Corporation, Armonk, NY (US)

(72) Inventors: Anton Robert, Igny (FR); Panagiotis Barkoutsos, Zurich (CH); Stefan Woerner, Zürich (CH); Ivano Tavernelli, Wädenswil (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 751 days.

(21) Appl. No.: 16/526,382

(22) Filed: Jul. 30, 2019

(65) Prior Publication Data

US 2021/0035003 A1    Feb. 4, 2021

(51) Int. Cl.
*G06N 10/00* (2022.01)
*G16C 10/00* (2019.01)

(52) U.S. Cl.
CPC ............. *G06N 10/00* (2019.01); *G16C 10/00* (2019.02)

(58) Field of Classification Search
None
See application file for complete search history.

(56) References Cited

U.S. PATENT DOCUMENTS

| 8,604,944 | B2 | 12/2013 | Berkley et al. |
| 2008/0052055 | A1 | 2/2008 | Rose et al. |
| 2009/0070402 | A1 | 3/2009 | Rose et al. |
| 2015/0220681 | A1* | 8/2015 | Dixit ....................... G06F 17/10 703/1 |
| 2018/0052979 | A1 | 2/2018 | Bito et al. |
| 2020/0082904 | A1* | 3/2020 | Uemura .................. G16B 50/00 |
| 2020/0364601 | A1* | 11/2020 | Yamazaki .............. G06N 5/003 |

OTHER PUBLICATIONS

Brest et al., Self-Adapting Control Parameters in Differential Evolution: A Comparative Study on Numerical Benchmark Problems. IEEE Transactions on Evolutionary Computation 19, 646 (2006). 12 pages.

(Continued)

*Primary Examiner* — Jany Richardson
(74) *Attorney, Agent, or Firm* — Amin, Turocy & Watson, LLP

(57) ABSTRACT

Techniques regarding determining a three-dimensional structure of a heteropolymer are provided. For example, one or more embodiments described herein can comprise a system, which can comprise a memory that can store computer executable components. The system can also comprise a processor, operably coupled to the memory, and that can execute the computer executable components stored in the memory. The computer executable components can comprise a polymer folding component that can generate a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

20 Claims, 14 Drawing Sheets

(56) References Cited

OTHER PUBLICATIONS

Piana, et al. "Assessing the accuracy of physical models used in protein-folding simulations:quantitative evidence from long molecular dynamics simulations." Current Opinion in Structural Biology. vol. 24, Feb. 2014, pp. 98-105. 8 pages.
"Enhancing Hybrid Quantum-Classical Algorithms for Optimization" U.S. Appl. No. 16/151,444, filed Oct. 4, 2018.
Mell, Peter, et al. "The NIST Definition of Cloud Computing." National Institute of Standards and Technology. Sep. 2011. 7 pages.
Babbush et al. "Construction of Energy Functions for Lattice Heteropolymer Models: A Case Study in Constraint Satisfaction Programming and Adiabatic Quantum Optimization" Advances in Chemical Physics: vol. 155 (2013) arXiv:1211.3422v2 [quant-ph]. 44 pages.
Chen et al. "Evolvability and Single-Genotype Fluctuation in Phenotypic Properties: A Simple Heteropolymer Model" Biophysical Journal vol. 98, Issue 11, Jun. 2, 2010, pp. 2487-2496. 10 pages.
Perdomo et al. "On the construction of model Hamiltonians for adiabatic quantum computation and its application to finding low energy conformations of lattice protein models" arXiv:0801.3625v2 Physical Review A 78 (2008). 35 pages.
Babej, et al. "Coarse-grained lattice protein folding on a quantum annealer" (2018). arXiv:1811.00713. 12 pages.
Babej, et al. "A quantum alternating operator ansatz with hard and soft constraints for lattice protein folding," (2018), airXiv:1810.13411. 12 pages.
Nannicini, "Performance of hybrid quantum/ classical variational heuristics for combinatorial optimization" arXiv:1805.12037 [quant-ph] (2018). 15 pages.
Zwanzig et al., "Levinthal's paradox" Proceedings of the National Academy of Sciences 89, 20 (1992). 3 pages.
Schram et al., "Exact enumeration of self-avoiding walks" Journal of Statistical Mechanics: Theory and Experiment 2011, P06019 (2011), arXiv:1104.2184. 6 pages.
Kmiecik et al., "Coarse-Grained Protein Models and Their Applications" Chemical Reviews 116, 7898 (2016). 39 pages.
Feynman et al. "Simulating Physics with Computers." International Journal of Theoretical Physics, vol. 21, Nos. 6/7, 1982. 22 pages.
Feynman "The Feynman Lectures on Physics 3 Volume Set)Set v." Addison-Wesley Publishing Company, Inc. 1970. 1376 pages.
Abrams et al., "A quantum algorithm providing exponential speed increase for finding eigenvalues and eigenvectors" Phys. Rev. Lett. 83, 5162 (1999). 9 pages.
Lloyd, "Universal Quantum Simulators" Science, New Series, vol. 273, No. 5278, pp. 1073-1078 American Association for the Advancement of Science, (1996). 7 pages.
Aspuru-Guzik et al., "Simulated Quantum Computation of Molecular Energies" Science 309, 1704 (2005). 21 pages.
O'Malley. "Scalable Quantum Simulation of Molecular Energies." Physical Review X 6, 031007 (2016). 13 pages.
Colless et al., "Computation of Molecular Spectra on a Quantum Processor with an Error-Resilient Algorithm" Phys. Rev. X 8, 011021 (2018). 7 pages.
Hempel et al., "Quantum Chemistry Calculations on a Trapped-Ion Quantum Simulator" arXiv:1803.10238 (2018). 22 pages.
Kandala et al., "Hardware-efficient Variational Quantum Eigensolver for Small Molecules and Quantum Magnets" Nature 549, 242 (2017). 24 pages.
Moll et al., "Quantum optimization using variational algorithms on near-term quantum devices" arXiv preprint arXiv:1710:01022 (2017) 18 pages.
Albash et al., "Finite temperature quantum annealing solving exponentially small gap problem with non-monotonic success probability" arXiv:1705.07452. 8 pages.
Ronnow et al., "Defining and detecting quantum speedup" Science 345, 420 (2014), arXiv: 1404.210. 15 pages.
Smolin et al., "Classical signature of quantum annealing" Frontiers in Physics 2, 52 (2014). 9 pages.
Hinds et al., "Exploring Conformational Space with a Simple Lattice Model for Protein Structure" Journal of Molecular Biology 243, 668 (1994). 15 pages.
Park et al., "Energy Functions that Discriminate X-ray and Nea-native Folds from Well-constructed Decoys" Journal of Molecular Biology 249, 493 (1995). 26 pages.
Kempe et al. "The Complexity of the Local Hamiltonian Problem." SIAM Journal of Computing, vol. 35(5), p. 1070-1097 (2006), conference version in Proc. 24th FSTTCS, p. 372-383 (2004). 30 pages.
Barkoutsos et al., "Fermionic Hamiltonians for quantum simulations: a general reduction scheme" arXiv:1706 03637 (2017). 6 pages.
Levitt et al., "Computer simulation of protein folding" Nature 253, 694 (1975). 5 pages.
Hinds et al., "A lattice model for protein structure prediction at low resolution" Proceedings of the National Academy of Sciences, 89,2536 (1992). 5 pages.
Shakhnovich et al., "Proteins with Selected Sequences Fold into Unique Native Conformation" Physical Review Letters 74, 2618 (1995). 5 pages.
Onuchic et al., "Theory of Protein Folding" Current Opinion in Structural Biology 14, 70 (2004). 6 pages.
Lindorff-Larsen et al., "How Fast-Folding Proteins Fold" Science 334, 517 (2011). 5 pages.
Hyeon et al., "Capturing the essence of folding and functions of biomolecules using coarse-grained models" Nature Communications 2, 487 (2011). 11 pages.
Unger et al., "Finding the Lowest Free Energy Conformation of a Protein is an NP-Hard Problem: Proof and Implications" Bulletin of Mathematical Biology 55, 1183, (1993). 16 pages.
Berger et al., "Protein Folding in the Hydrophobic-Hydrophilic (HP) Model is NP-Complete" Journal of Computational Biology 5, 27 (1998). 10 pages.
Mandra et al., "A deceptive step towards quantum speedup detection" Quantum Science and Technology 3, 04LT01 (2018), arXiv: 1711.01368. 11 pages.
King et al., "Quantum Annealing amid Local Ruggedness and Global Frustration" arXiv:1701.04579 [quant-ph] (2017). 17 pages.
Streif et al., "Comparison of QAOA with Quantum and Simulated Annealing" arXiv:1901.01903 [quant-ph] (2019). 6 pages.
Preskill, "Quantum Computing in the NISQ era and beyond" arXiv:1801.00862 [cond-mat, physics:quant-ph] (2018). 20 pages.
Levinthal, "Are there pathways for protein folding?" Journal de Chimie Physique, 44 (1968). 2 pages.
Onuchic et al., "Toward an outline of the topography of a realistic protein-folding funnel" Proceedings of the National Academy of Sciences 92, 3626 (1995). 5 pages.
Duan, "Pathways to a Protein Folding Intermediate Observed in a 1-Microsecond Simulation in Aqueous Solution" Science 282, 740 (1998). 6 pages.
Cai, et al., "A practical heuristic for finding graph minors" arXiv:1406.2741 [quant-ph] (2014). 16 pages.
Perdomo-Ortiz et al, "Finding low-energy conformations of lattice protein models by quantum annealing" Scientific Reports 2 (2012). 10.1038/strep00571. 7 pages.
Farhi et al., "Quantum Supremacy through the Quantum Approximate Optimization Algorithm" arXiv:1602.07674 [quant-ph] (2016). 22 pages.
Miyazawa et al, "Residue-Residue Potentials with a Favorable Contact Pair Term and an Unfavorable High Packing Density Term, for Simulation and Threading" Journal of molecular biology 256, 623 (1996). 22 pages.
Peruzzo,et al., "A variational eigenvalue solver on a photonic quantum processor" Nat Commun 5 (2014), 10.1038/ncomms5213. 7 pages.
McClean et al., "The theory of variational hybrid quantum-classical algorithms" New J. Phys. 18, 023023 (2016). 23 pages.
Hadfield et al., "From the Quantum Approximate Optimization Algorithm to a Quantum Alternating Operator Ansatz" Algorithms 12, 34 (2019). arXiv:1709.03489. 45 pages.

(56) References Cited

OTHER PUBLICATIONS

Aleksandrowicz et al., "Qiskit: An open-source framework for quantum computing." 110.5281/zenodo.2562110. Last Accessed Jul. 1, 2019. 4 pages.

Das et al., "Recent Advances in Differential Evolution—An Updated Survey" Swarm and Evolutionary Computation 27, 1 (2016). 63 pages.

* cited by examiner

BRANCHED HETEROPOLYMER LATTICE MODEL FOR QUANTUM OPTIMIZATION

BACKGROUND

The subject disclosure relates to one or more models that can determine the three-dimensional structure of a heteropolymer, and more specifically, course-grain lattice models that can be implemented via one or more quantum computers and/or optimized via one or more classical computing algorithms.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses and/or computer program products that determine one or more three-dimensional structures of heteropolymers are described.

According to an embodiment, a system is provided. The system can comprise a memory that can store computer executable components. The system can also comprise a processor, operably coupled to the memory, and that can execute the computer executable components stored in the memory. The computer executable components can comprise a polymer folding component that can generate a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

According to an embodiment, a computer-implemented method is provided. The computer-implemented method can comprise generating, by a system operatively coupled to a processor, a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

According to an embodiment, a computer program product for determining a folding of a polymer chain is provided. The computer program product can comprise a computer readable storage medium having program instructions embodied therewith. The program instructions can be executable by a processor to cause the processor to generate, by the processor, a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

DETAILED DESCRIPTION

Figure 1:
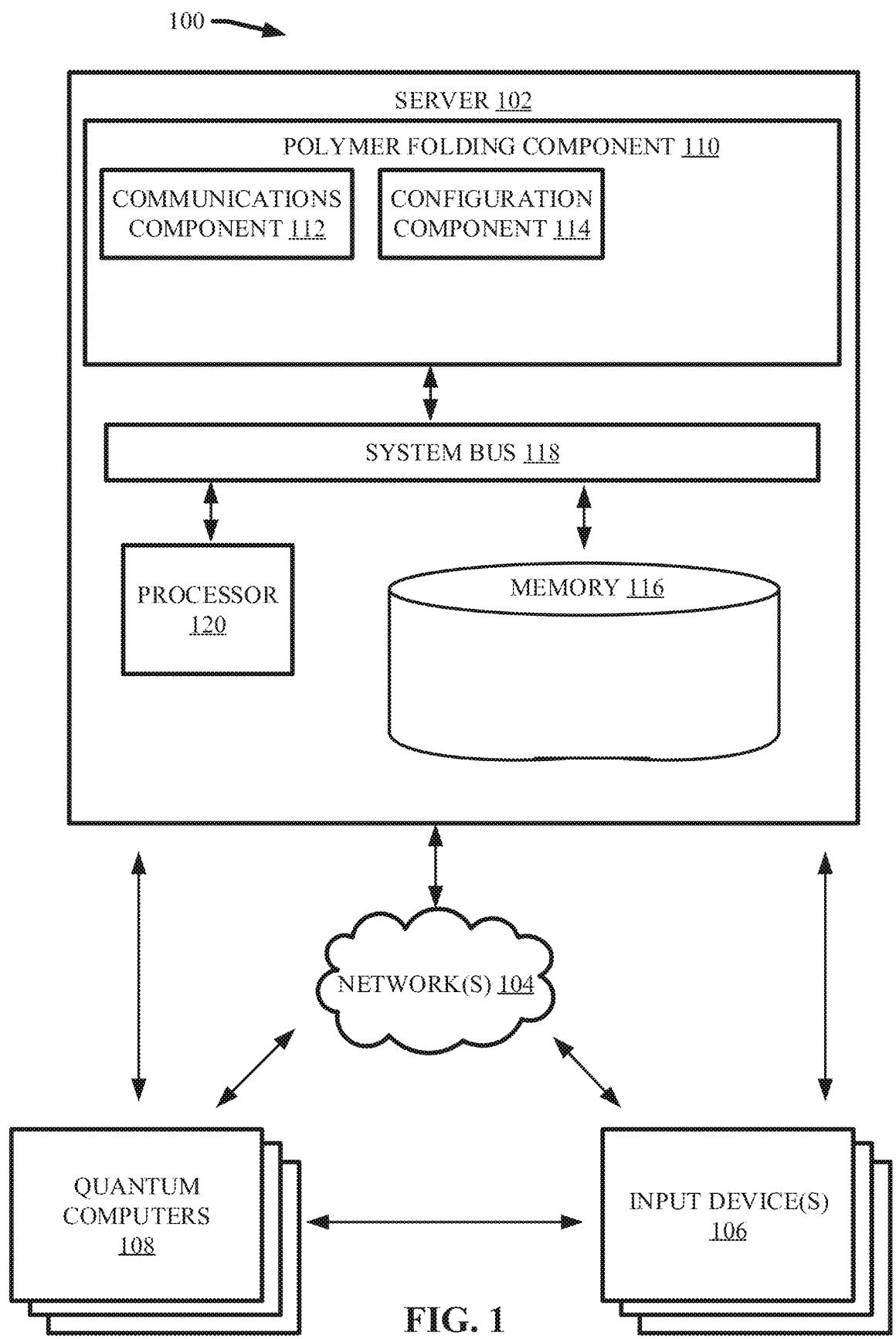
FIG. 1 illustrates a block diagram of an example, non-limiting system that can generate one or more course-grain lattice models to determine the three-dimensional structure of a heteropolymer in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Polymer chain folding can be a prototype model for analyzing protein folding, misfolding, and/or unfolding. Predicting the three-dimensional ("3D") structure of a protein from its primary sequence of amino acids is known as the protein folding problem. A heteropolymer's (e.g., a protein's) 3D structure can play an important role in chemistry, biology, and/or medical applications (e.g., in chemical compound discovery). Although classical algorithms provide practical solutions for the sampling of the conformation space of small proteins, they cannot tackle the intrinsic NP-hard complexity of the problem, even when reduced to its simplest Hydrophobic-Polar model. There has been evidences that quantum algorithms can be successfully used to accelerate energy optimization in frustrated systems on Noisy Intermediate-Scale Quantum Computers ("NISQ").

Various embodiments of the present invention can be directed to computer processing systems, computer-implemented methods, apparatus and/or computer program products that facilitate the efficient, effective, and autonomous (e.g., without direct human guidance) generation of one or more models and quantum algorithms for the folding of a polymer chain on a lattice that can scale with the number of monomers comprising the polymer chain (e.g., can scale in $N^4$, wherein N is the number of monomers). For example, the one or more models can reflect one or more physico-chemical properties of the subject polymer (e.g., a protein), thereby reducing the gap between coarse-grained representations and mere lattice models. Further, one or more embodiments described herein can utilize a versatile optimization scheme, combining variational quantum algorithms specifically adapted to classical cost functions and evolutionary strategies to simulate the folding conformations of the heteropolymers.

In various embodiments, one or more embodiments can generate one or more coarse-grained models for protein folding that can be suited for the representation of branched heteropolymers comprising "N" monomers on a lattice (e.g., a tetrahedral lattice). For example, a two-centered coarse-grained description of monomers (e.g., backbone and side chain) can be used to mimic the heteropolymer sequence. Further, the monomers of the heteropolymers can be depicted by one or more beads having a defined number of shades corresponding to different physical properties (e.g., hydrophobicity and/or charge).

The computer processing systems, computer-implemented methods, apparatus and/or computer program products employ hardware and/or software to solve problems that are highly technical in nature (e.g., determining the three-dimensional structure of a heteropolymer), that are not abstract and cannot be performed as a set of mental acts by a human. For example, an individual, or a plurality of individuals, cannot readily determine the vast amounts of configurations that can characterize a heteropolymer and analyze the associate energies of conformation. Additionally, an individual cannot utilize quantum-mechanical phenomena to determine heteropolymer configurations as performed by one or more embodiments described herein.

FIG. 1 illustrates a block diagram of an example, non-limiting system 100 that can generate one or more coarse-grain models to determine a three-dimensional structure of a heteropolymer. Repetitive description of like elements employed in other embodiments described herein is omitted for sake of brevity. Aspects of systems (e.g., system 100 and the like), apparatuses or processes in various embodiments of the present invention can constitute one or more machine-executable components embodied within one or more machines, e.g., embodied in one or more computer readable mediums (or media) associated with one or more machines. Such components, when executed by the one or more machines, e.g., computers, computing devices, virtual machines, etc. can cause the machines to perform the operations described.

As shown in FIG. 1, the system 100 can comprise one or more servers 102, one or more networks 104, input devices 106, and/or quantum computers 108. The server 102 can comprise polymer folding component 110. The polymer folding component 110 can further comprise communications component 112 and/or configuration component 114. Also, the server 102 can comprise or otherwise be associated with at least one memory 116. The server 102 can further comprise a system bus 118 that can couple to various components such as, but not limited to, the polymer folding component 110 and associated components, memory 116 and/or a processor 120. While a server 102 is illustrated in FIG. 1, in other embodiments, multiple devices of various types can be associated with or comprise the features shown in FIG. 1. Further, the server 102 can communicate with one or more cloud computing environments.

The one or more networks 104 can comprise wired and wireless networks, including, but not limited to, a cellular network, a wide area network (WAN) (e.g., the Internet) or a local area network (LAN). For example, the server 102 can communicate with the one or more input devices 106 and/or quantum computers 108 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like. Further, although in the embodiment shown the polymer folding component 110 can be provided on the one or more servers 102, it should be appreciated that the architecture of system 100 is not so limited. For example, the polymer folding component 110, or one or more components of polymer folding component 110, can be located at another computer device, such as another server device, a client device, etc.

The one or more input devices 106 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. A user of the system 100 can utilize the one or more input devices 106 to input data into the system 100, thereby sharing (e.g., via a direct connection and/or via the one or more networks 104) said data with the server 102 and/or quantum computers 108. For example, the one or more input devices 106 can send data to the communications component 112 (e.g., via a direct connection and/or via the one or more networks 104). Additionally, the one or more input devices 106 can comprise one or more displays that can present one or more outputs generated by the system 100 to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

A user of the system 100 can utilize the one or more input devices 106 and/or the one or more networks 104 to input one or more settings and/or commands into the system 100. For example, in the various embodiments described herein, a user of the system 100 can operate and/or manipulate the server 102 and/or associate components via the one or more input devices 106. Additionally, a user of the system 100 can utilize the one or more input devices 106 to display one or more outputs (e.g., displays, data, visualizations, and/or the like) generated by the server 102 and/or associate components. Further, in one or more embodiments, the one or more input devices 106 can be comprised within, and/or operably coupled to, a cloud computing environment. In various embodiments, a user of the system 100 can provide the polymer folding component 110 with The one or more quantum computers 108 can execute one or more quantum computer programs to make direct use of distinctively quantum mechanical phenomena, such as superposition and/or entanglement, to perform operations on data. The one or more quantum computers 108 can comprise quantum computers 108 characterized by respective parameters. Example parameters can include, but are not limited to: a quantum computer's 108 qubit configuration (e.g., including the number, connectivity, and/or properties of qubits comprised within the quantum computer 108), the construction type of a quantum computer 108 (e.g., whether a subject quantum computer is an adiabatic quantum computer, a cluster-state quantum computer, or a gate-based quantum computer), a quantum computer's 108 quantum gate configuration (e.g., including the number, type, position, and/or connectivity of quantum gates included in the subject quantum computer 108), a combination thereof, and/or the like. Example types of quantum computers 108 can include, but are not limited to: atom trap quantum computers, nuclear magnetic resonance quantum computers, photonic quantum computers, quantum dot quantum computers, and/or superconductor quantum computers.

In one or more embodiments, the communications component 112 can receive monomer data from the one or more input devices 106 (e.g., via a direct electrical connection and/or through the one or more networks 104) and share the data with the various associate components of the polymer folding component 110. The monomer data can regard one or more of the monomers comprised within a subject heteropolymer. Example monomer data that can be entered via the one or more input devices 106 can include, but is not limited to: the chemical structure of the monomers, the identity of the monomers, the number of monomers, physical properties of the monomers, chemical properties of the monomers, interaction strength between different monomers, a combination thereof, and/or the like.

The configuration component 114 can encode a configuration of a heteropolymer to a first qubit registry of the one or more quantum computers 108. In various embodiments, the configuration component 114 can encode the configuration in relation to a lattice model. For example, the heteropolymer configuration can be grown on the lattice by adding beads representing the monomers comprised within the heteropolymer, and/or encoding in the first qubit registry different turns that can define the position of a bead relative to a previously added bead.

The lattice can comprise two or more non-equivalent sets of lattice points, wherein each set of lattice points can be associated with a set of directions that can facilitate a turn exhibited in the monomer sequence from one monomer to another. For example, the lattice can comprise two sets of alternating lattice points, wherein a first set of lattice points can be associated with beads (e.g., monomers) located at an even position along the monomer sequence (e.g., the second monomer, the fourth monomer, etc.) while a second set of lattice points can be associated with beads (e.g., monomers) located at an odd position along the monomer sequence (e.g., the first monomer, the third monomer, etc.). Moreover, the monomer sequence can be characterized by a set of turns associated with each set of directions (e.g., a first set of turns can be associated with a first set of directions and/or a second set of turns can be associated with a second set of directions). The configuration component 114 can assign a qubit for each direction of a set of directions associated with a lattice point to encode a turn in the monomer sequence stemming from the lattice point.

For example, in one or more embodiments the lattice can have a tetrahedral geometry, comprising a first and second set of alternating lattice points. At lattice points of the first set, the heteropolymer can grow along a first set of four directions (e.g., directions "0", "1", "2", and/or "3"). At lattice points of the second set, the heteropolymer can grow along a second set of four directions (e.g., directions "$\bar{0}$", "$\bar{1}$", "$\bar{2}$", and/or "$\bar{3}$"). Further, the first set of lattice points can be located at even positions along the monomer sequence (e.g., the second monomer, the fourth monomer, etc.) while the second set of lattice points can be points located at odd positions along the monomer sequence (e.g., the first monomer, the third monomer, etc.). The configuration component 114 can set a first turn of the monomer sequence (e.g., represented by "$t_1$") to direction $\bar{1}$ (e.g., $t_1 = \bar{1}$), and a second turn of the monomer sequence (e.g., represented by "$t_2$") to direction 0 (e.g., $t_2 = 0$). Thereby, the configuration component 114 can encode subsequent turns (e.g., represented by "$t_i$", wherein "i" denotes a backbone monomer in the primary sequence of the heteropolymer) of the monomer sequence by assigning a qubit per possible direction stemming from a lattice point (e.g., $t_1 = q_{4i-3} q_{4i-2} q_{4i-1} q_{4i}$). The total number of qubits utilized by the configuration component 114 to encode a conformation can be characterized by Equation 1 below.

$$N_{cf} = 4(N-3) \quad (1)$$

Wherein "$N_{cf}$" can represent the number of configuration qubits to encode a conformation, and "N" can represent the number of monomers comprised within the heteropolymer, wherein each monomer can be represented by one bead comprised within the lattice model. Wherein the beads of the lattice can represent two or more monomers, Equation 1 can be adapted by replacing "N" with the total number of beads in the lattice.

In various embodiments, the configuration component 114 can encode the first qubit registry via a sparse encoding scheme or a dense encoding scheme. For example, wherein the configuration component 114 encodes turns on a tetrahedral lattice, the configuration component 114 can encode the conformation to the first qubit registry via a sparse encoding scheme using four qubits (e.g., "$q_{4i-3}q_{4i-2}q_{4i-1}q_{4i}$"), with one qubit per possible direction. Further, one of the qubits can be equal to one. Additionally, the configuration component 114 can encode the turns in a given side chain of the heteropolymer structure via the first qubit registry in accordance with the general formula: $q_{(1)}^{(0)}q_{(1)}^{(1)}q_{(1)}^{(2)}q_{(1)}^{(3)}, q_{(2)}^{(0)}q_{(2)}^{(1)}q_{(2)}^{(2)}q_{(2)}^{(3)} \ldots$ For instance, the configuration component 114 can set the first two turns to "0010" and "0001", wherein a string of qubits defining an exemplary conformation can have the following form (e.g., wherein the side chain qubits can be in parentheses):

$$0100(q_{2(1)}^{(1)}q_{2(1)}^{(2)}q_{2(1)}^{(3)} \ldots )1000(q_{3(1)}^{(1)}q_{3(1)}^{(2)}q_{3(1)}^{(3)}q_{3(1)}^{(4)} \ldots )$$
$$q_9q_{10}q_{11}q_{12} \cdots q_{4(N-1)-3}q_{4(N-1)-2}q_{4(N-1)-1}q_{4(N-1)}$$

Wherein the number of configuration qubits comprised within the first qubit registry utilized by the configuration component 114 can be characterized by Equation 2 below.

$$4(N-1)-8=4(N-3) \quad (2)$$

In another example, wherein the configuration component 114 encodes turns on a tetrahedral lattice, the configuration component 114 can encode the conformation to the first qubit registry via a dense encoding scheme using two qubits (e.g., "$q_{2i-1}q_{2i}$"). Further, the configuration component 114 can encode turns in a given side chain of the heteropolymer structure via the first qubit registry in accordance with the general formula: $q_{i(1)}^{(1)}q_{i(1)}^{(2)}, q_{i(2)}^{(1)}q_{i(2)}^{(2)} \ldots$ For instance, the configuration component 114 can set the first two turns to "01" and "00"; wherein if the second bead does not bear a side chain, another qubit can be saved without breaking symmetry (e.g., $q_6=1$). Thereby, a string of qubits defining an exemplary conformation can have the following form (e.g., wherein the side chain qubits can be in parentheses):

$$01(q_{2(1)}^{(1)}q_{2(1)}^{(2)} \ldots )00(q_{3(1)}^{(1)}q_{3(1)}^{(2)} \ldots )q_5q_6(q_{4(1)}^{(1)}q_{4(1)}^{(2)} \ldots )q_7q_8 \cdots q_{2(N-1)-1}q_{2(N-1)}$$

Wherein the number of configuration qubits comprised within the first qubit registry utilized by the configuration component 114 can be characterized by Equation 3 below.

$$2(N-1)-4=2(N-3) \quad (3)$$

Additionally, the configuration component 114 can introduce an indicator of the direction chosen at a subject turn. For example, the configuration component 114 can denote $f_a(q_{2i-1}, q_{2i})=f_a(i)$, wherein the function can return a value of 1 if the direction "a" is chosen at a given turn. For instance, the direction indication in the dense encoding scheme can be characterized by Equations 4-7 below.

$$f_0(i)=(1-q_{2i-1})(1-q_{2i}) \quad (4)$$

$$f_1(i)=q_{2i}(q_{2i}-q_{2i-1}) \quad (5)$$

$$f_2(i)=q_{2i-1}(q_{2i-1}-q_{2i}) \quad (6)$$

$$f_3(i)=q_{2i-1}q_{2i} \quad (7)$$

Further, the direction indication in the sparse encoding scheme can be characterized by Equations 8-11 below.

$$f_0(i)=q_{4i-3} \quad (8)$$

$$f_1(i)=q_{4i-2} \quad (9)$$

$$f_2(i)=q_{4i-1} \quad (10)$$

$$f_3(i)=q_{4i} \quad (11)$$

Figure 2A:
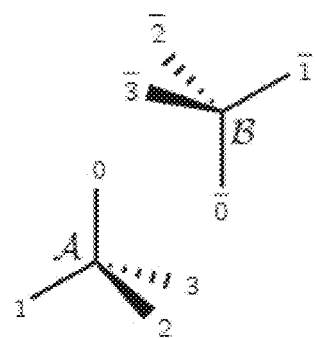
FIG. 2A illustrates a diagram of example, non-limiting lattice points that can be encoded into a qubit registry to determine a polymer folding conformation in accordance with one or more embodiments described herein.

FIG. 2A illustrates a diagram of example, non-limiting sets of lattice points that can be utilized by the configuration component 114 to encode one or more conformations to the first qubit registry in accordance with one or more embodiments described herein. Repetitive description of like elements employed in other embodiments described herein is omitted for sake of brevity. In various embodiments, the two sets of lattice points depicted in FIG. 2A can be utilized in a tetrahedral lattice model. As shown in FIG. 2A, a first set of lattice points (e.g., represented by "A" in FIG. 2A) can be a point of origin for four possible turn directions (e.g., represented by "0", "1", "2", and "3") in a tetrahedral molecular geometry. Likewise, a second set of lattice points (e.g., represented by "B" in FIG. 2A) can be a point of origin for four possible turn directions (e.g., represented by "$\overline{0}$", "$\overline{1}$", "$\overline{2}$", and "$\overline{3}$") in a tetrahedral molecular geometry.

Figure 2B:
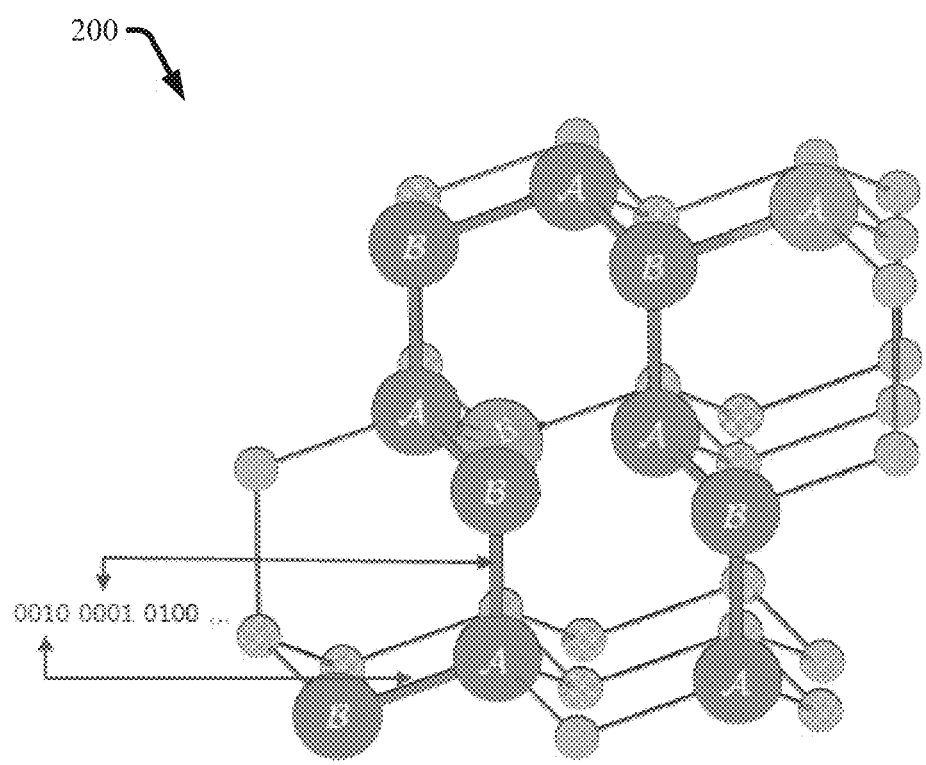
FIG. 2B illustrates a diagram of an example, non-limiting tetrahedral lattice that can encode one or more turning points between lattices points representing a configuration of a heteropolymer in accordance with one or more embodiments.

FIG. 2B illustrates a diagram of an example, non-limiting tetrahedral lattice geometry 200 that can be utilized by the configuration component 114 to encode one or more conformations to the first qubit registry in accordance with one or more embodiments described herein. Repetitive description of like elements employed in other embodiments described herein is omitted for sake of brevity. In various embodiments, the polymer folding component 110 can be motivated to utilize a lattice having a tetrahedral geometry by the chemical plausibility of the angles enforced by the lattice (e.g., 109.47° for bond angles, 180° or 60° for dihedrals), which can allow an all-atom description for a wide range of chemical and biological compounds.

As shown in FIG. 2B, the exemplary tetrahedral lattice geometry can comprise the exemplary first and second sets of lattice points depicted in FIG. 2A. For example, each point on the tetrahedral lattice geometry 200 can be comprised within the first set of lattice points or the second set of lattice points. As shown in FIG. 2B, the large spheres labeled as an "A" lattice point or a "B" lattice point can be beads representing one or more monomers comprised within the heteropolymer structure. Further, the bonds between adjacent beads can be formed along one of the possible turn directions, and can delineate the turns in the heteropolymer's structure from monomer to monomer that can be encoded by the configuration component 114. For example, FIG. 2B depicts an exemplary value string that can be encoded to the first qubit registry to represent the first two turns of the monomer sequence developed on the exemplary tetrahedral lattice geometry 200.

Additionally, the beads can be distinguished (e.g., shaded) to delineate different physical and/or chemical properties. For example, the varying shading of the beads shown in the exemplary tetrahedral lattice geometry 200 can delineate beads comprised within the backbone structure of the heteropolymer from beads comprised within one or more side chain structures of the heteropolymer. Thereby, one or more three-dimensional structures of the heteropolymer can be developed on the lattice from lattice point to lattice point (e.g., as shown in the three-dimensional structure of a heteropolymer comprising a 10 monomer backbone developed on the tetrahedral lattice geometry 200 of FIG. 2B).

Figure 3:
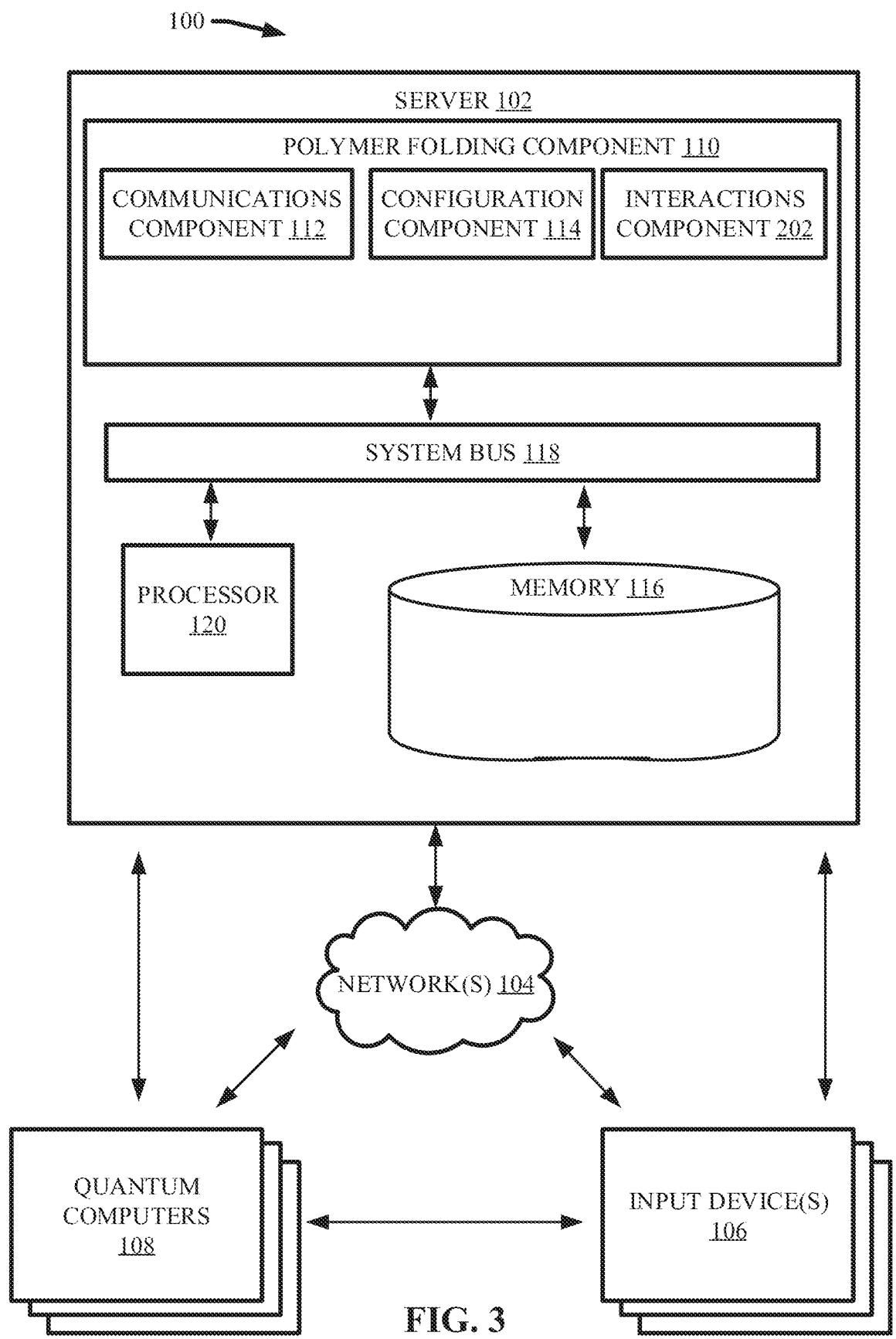
FIG. 3 illustrates a block diagram of an example, non-limiting system that can determine one or more interaction distances between monomers of a heteropolymer in accordance with one or more embodiments described herein.

FIG. 3 illustrates a diagram of the example, non-limiting system 100 further comprising interactions component 302 in accordance with one or more embodiments described herein. Repetitive description of like elements employed in other embodiments described herein is omitted for sake of brevity. In various embodiments, the interactions component 302 can encode one or more interaction distances between monomers comprised within the heteropolymer to a second qubit registry of the one or more quantum computers 108. For example, the interactions component 302 can determine one or more interaction distances between given monomers of the heteropolymer based, at least in part, on the turns encoded by the configuration component 114 (e.g., the states of the configuration qubits of the first qubit registry).

In one or more embodiments, the one or more interaction distances can be special distances between two or more given monomers in a subject three-dimensional structure of the heteropolymer. The interactions component 302 can encode the one or more interaction distances with respect to the edges and/or diagonals of the lattice model. The number of interaction qubits from the second qubit registry that can be utilized by the interactions component 302 to encode the one or more interactions distances can depend on the structure of the heteropolymer (e.g., including the backbone and side chain structures). The nearest neighbor beads on the lattice can occupy positions on the lattice at different lattice point sets (e.g., an "A" lattice point or a "B" lattice point). In contrast, at greater interaction distances, monomers can interact with other monomers positioned at a lattice point comprised within the same set or a different set. For example, a monomer occupying a point comprised within a first lattice point set can interact with another monomer occupying another point comprised within the first lattice point set. In another example, the monomer occupying the point comprised within the first lattice point set can interact with another monomer occupy a point comprised within the second lattice point set.

In various embodiments, the pairwise interaction energies between the monomers (e.g., between the beads on the lattice) can be arbitrary defined by the interaction component 302 to reproduce a fold of interest, given a primary monomer sequence (e.g., as encoded by the configuration component 114 and/or developed on the lattice model). In some embodiments, the interaction component 302 can adapt the pairwise interaction energies from one or more pre-existing models.

In one or more embodiments, the interactions component 302 can determine the algebraic number of turns for an axis between a first bead (e.g., represented by "i") on the lattice model and a second bead (e.g., represented by "j") on the lattice model (e.g., wherein j>i), by adding all the turns from a first set of lattice points (e.g., "A" lattice points, which can correspond to even positions along the monomer sequence order) that have been made along the axis and subtract the turns from a second set of lattice points (e.g., "B" lattice points, which can correspond to odd positions along the monomer sequence order). Thereby, the interactions component 302 can denote the number of occurrences "a" (e.g., reps. "a") of turn encodings in the sequence between beads i and j in accordance with Equations 12 and 13 below.

$$\Delta n_a(i,j) = n_a(i,j) - \bar{n}_a(i,j) \tag{12}$$

$$\Delta n_a(i,j) = \Sigma_{k=i}^{j-1}(-1)^k f_a(k) \tag{13}$$

Wherein "k" can represent the number of intermediate beads between bead i and bead j (e.g., wherein the distance between beads i and j is being measured).

Additionally, the interaction distance between beads that are positioned on side chains of the heteropolymer (e.g., between the "$s^{th}$" bead on a side chain of i, represented by $i^{(s)}$, and the $p^{th}$ bead on the side chain of j, represented by $j^{(p)}$) can be determined by the interactions component 302 by considering the distance between beads i and j and then adding or removing the distance contributions of the side chains (e.g., encoded to side chain qubits in the first registry). Wherein j>I, the side chain qubits of j, can be taken into account by the interactions component 302 with a plus sign. Additionally, the interaction component 302 can determine the direction of the one or more side chains by the parity of i and j. For example, the interaction component 302 can determine the interaction distance between the side chain beads in accordance with Equation 14 below.

$$\Delta n_a(i^{(s)}, j^{(p)}) = \Delta n_a(i,j) + \Sigma_{l=1}^{p}(-1)^l f_a(j^{(l)}) - \Sigma_{m=1}^{s}(-1)^m f_a(i^{(m)}) \tag{14}$$

Wherein "l" and "m" can represent counters in the summation can range from 1 to p and m respectively.

In one or more embodiments, the interactions component 302 can further introduce a four dimensional vector in accordance with Equation 15 below.

$$x(i, j) = \begin{pmatrix} \Delta n_1(i, j) \\ \Delta n_2(i, j) \\ \Delta n_3(i, j) \\ \Delta n_4(i, j) \end{pmatrix} \tag{15}$$

For example, a bijective function between the possible values of $d(i, j) = \|x(i, j)\|_2^2$ and free space distances $r_{i,j}$ in a bond unit on the lattice (e.g., a tetrahedral lattice) in accordance with Equation 16 below.

$$d(i, j) = 0 \Rightarrow r_{ij} = 0 \tag{16}$$

$$d(i, j) = 1 \Rightarrow r_{ij} = 1$$

$$d(i, j) = 2 \Rightarrow r_{ij} = 2\sqrt{\frac{2}{3}} \approx 1.63$$

$$d(i, j) = 3 \Rightarrow r_{ij} = \sqrt{\frac{11}{3}} \approx 1.91$$

$$d(i, j) = 4 \Rightarrow r_{ij} = \frac{4}{\sqrt{3}} \approx 2.31$$

$$d(i, j) = 5 \Rightarrow r_{ij} = \sqrt{\frac{19}{3}} \approx 2.52$$

Wherein if d(I,j)=1, then beads i and j can be $1^{th}$ nearest neighbors on the lattice.

Figure 4A:
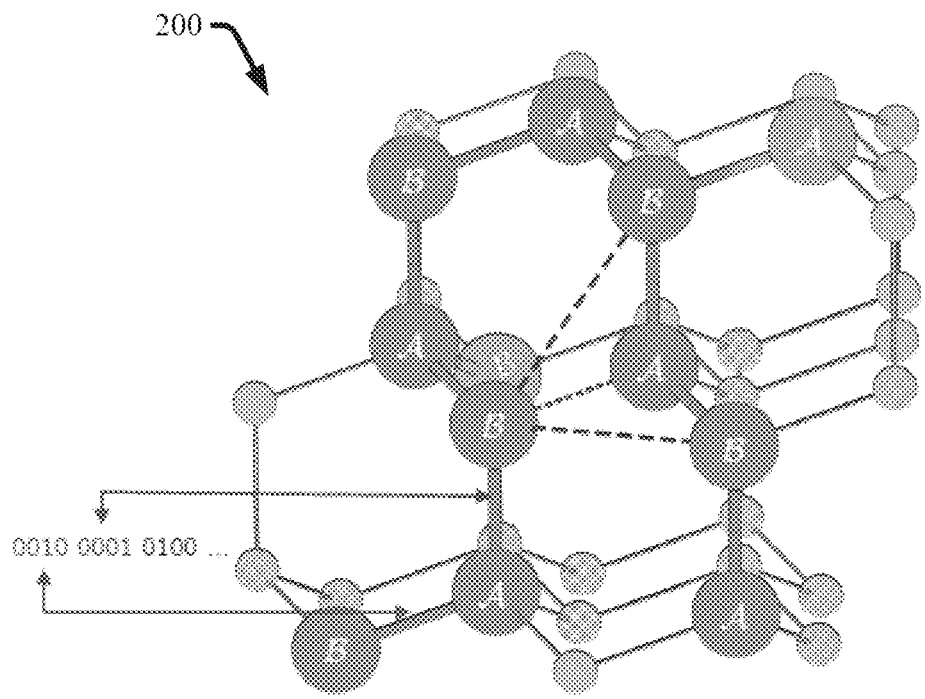
FIG. 4A illustrates a diagram of an example, non-limiting tetrahedral lattice that can account for one or more interaction distances between monomers of a heteropolymer in accordance with one or more embodiments described herein.

FIG. 4A illustrates a diagram of the example, non-limiting interaction distances on the exemplary tetrahedral lattice 200 that can be encoded by the interactions component 302 in accordance with one or more embodiments described herein. Repetitive description of like elements employed in other embodiments described herein is omitted for sake of brevity. For example, the dashed lines shown in FIG. 4A can represent interaction distances that can be encoded to the second qubit registry of the one or more quantum computers 108 by the interactions component 302, as described herein.

Figure 4B:
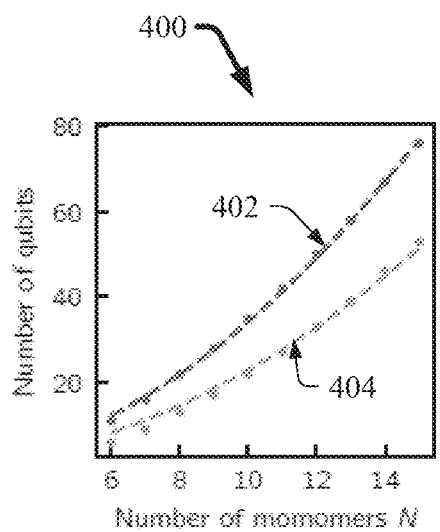
FIG. 4B illustrates a diagram of an example, non-limiting graph that can describe a relation between the number of qubits utilized to encode monomers of a heteropolymer in accordance with one or more embodiments described herein.
Figure 4C:
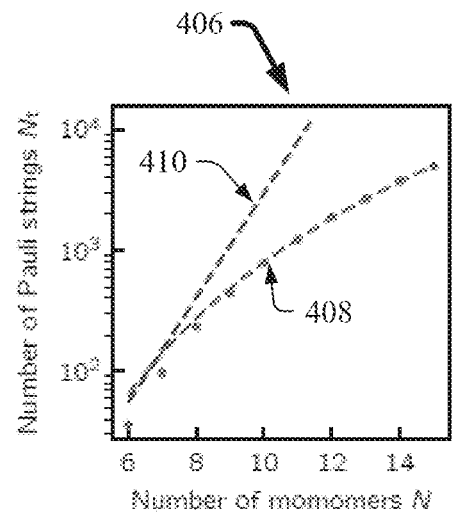
FIG. 4C illustrates a diagram of an example, non-limiting graph that can depict the efficacy of scaling a system that can generate one or more course-grain lattice models to determine the three-dimensional structure of a heteropolymer in accordance with one or more embodiments described herein.

FIGS. 4B and 4C illustrate diagrams of example, non-limiting graphs that can depict the scaling potential of the various functions of the configuration component 114 and/or the interactions component 302 in accordance with one or more embodiments described herein. Repetitive description of like elements employed in other embodiments described herein is omitted for sake of brevity. For example, graph 400 depicts a relationship between the number of qubits utilized in a 3-local term model (e.g., represented by line 402) using a dense encoding scheme and 5-local term model (e.g., represented by line 404) using a sparse encoding scheme and the number of monomers comprised within the heteropolymer. Additionally, graph 406 depicts scaling of the model for the terms of the qubit Hamiltonian, wherein the parameters of the fit are, for example, (a,b) (0.15, 1.49), wherein the parameters can be fitted to the function based on a numerical analysis. For instance, line 408 can be represent parameters of in fit in accordance with the function: $a(N-b)^4$; and line 410 can represent parameters of fit in accordance with the function: exp(N).

Figure 5:
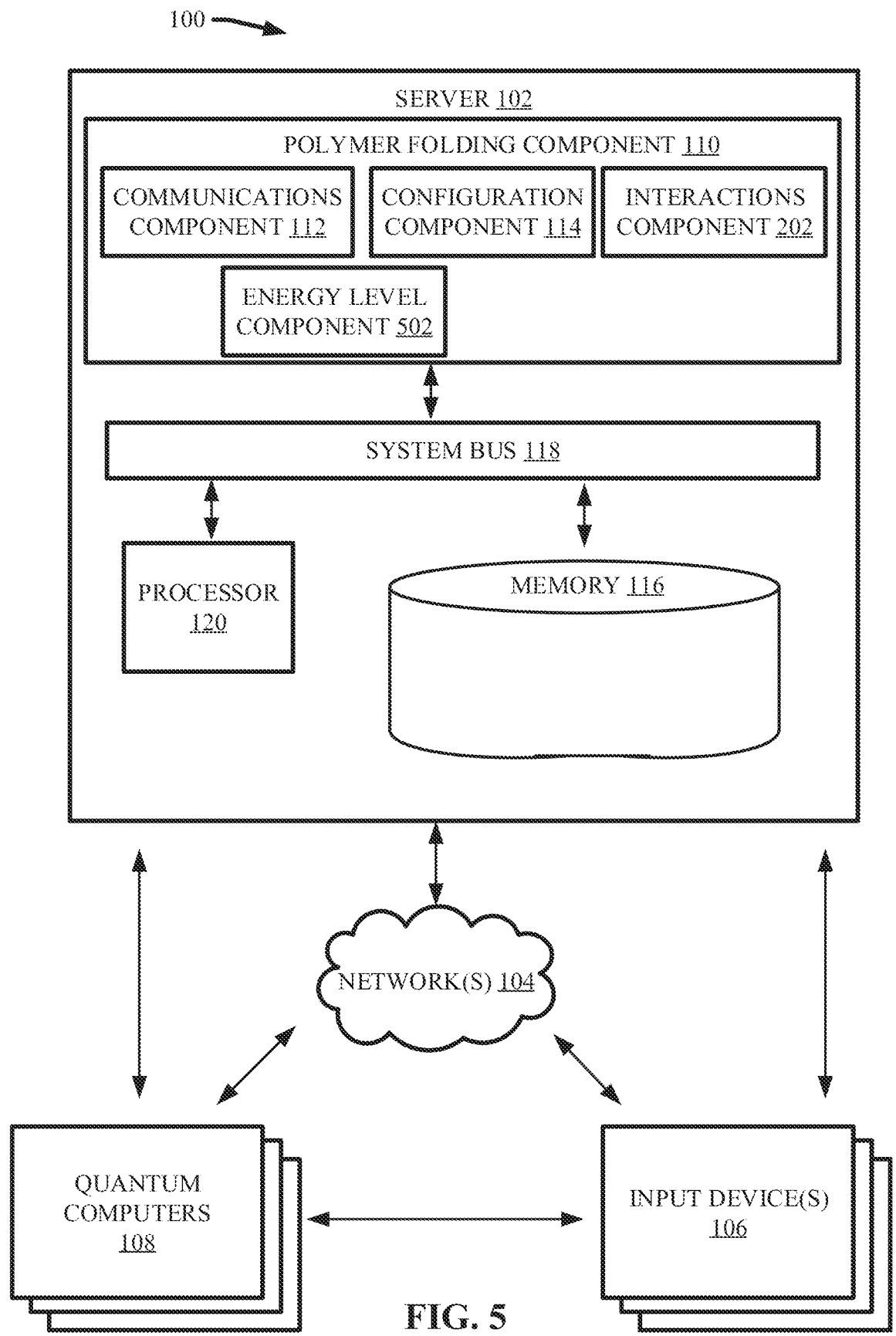
FIG. 5 illustrates a block diagram of an example, non-limiting system that can define one or more Hamiltonians that can describe an energy of conformation regarding a three-dimensional configuration of a heteropolymer in accordance with one or more embodiments.
Figure 6:
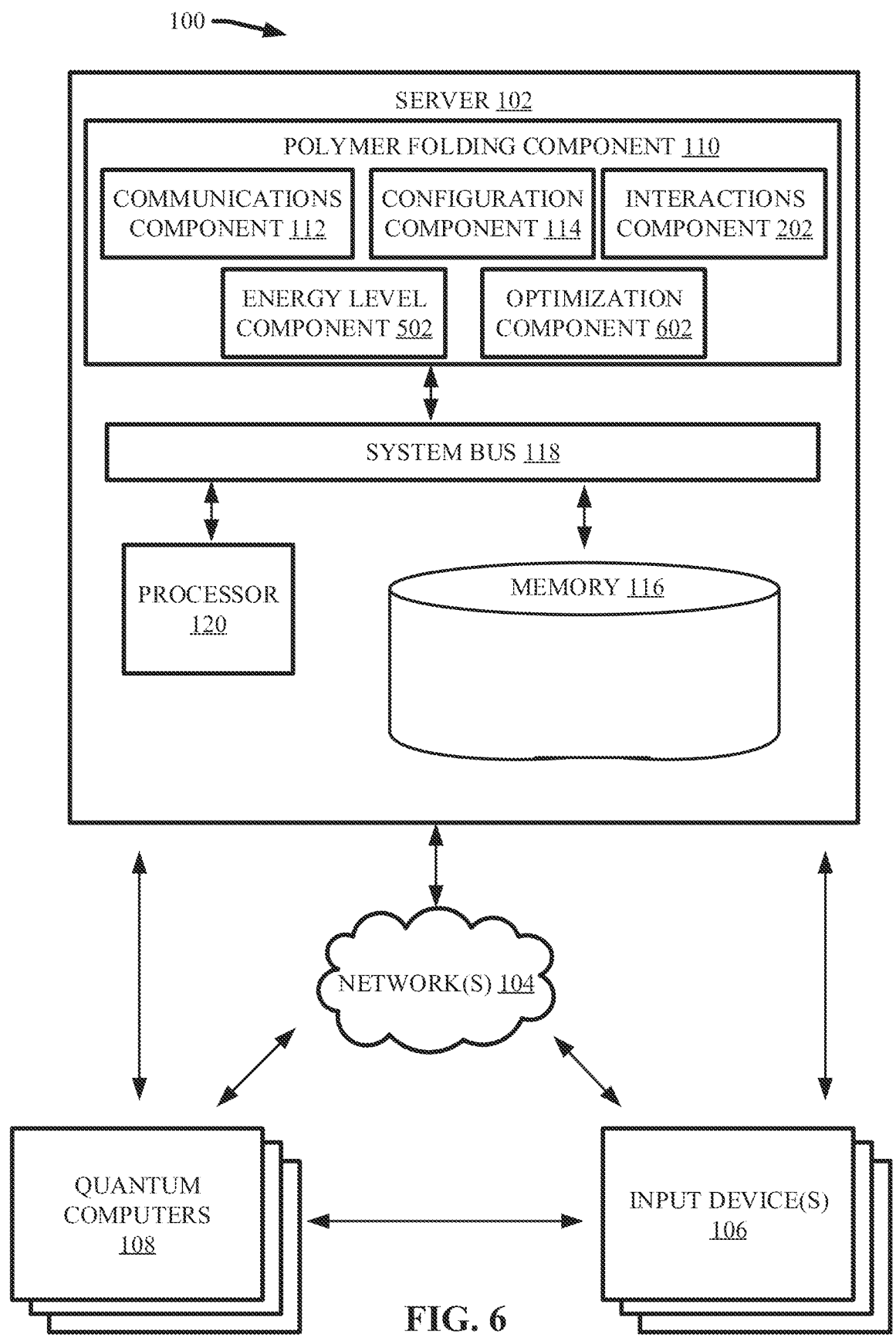
FIG. 6 illustrates a diagram of an example, non-limiting system that can determine one or more low-energy folding conformations that can characterize the three-dimensional structure of a heteropolymer in accordance with one or more embodiments described herein.

FIG. 5 illustrates a diagram of the example, non-limiting polymer folding component 110 further comprising energy level component 502 in accordance with one or more embodiments described herein. Repetitive description of like elements employed in other embodiments described herein is omitted for sake of brevity. In various embodiments, the energy level component 502 can define one or more qubit Hamiltonians that can describe one or more energies of conformations of the heteropolymer based on the sequence of monomers, turns, and/or interaction distances encoded to the first and/or second qubit registries by the configuration component 114 and/or interactions component 302.

In one or more embodiments, the energy level component 502 can define one or more qubit Hamiltonians that can describe the energy of a given fold of the heteropolymer by the sequence of beads on the lattice and encoded turns. The energy level component 502 can apply one or more penalty terms when physical constraints are violated (e.g., when beads occupy the same position on the lattice). Further, the energy level component 502 can apply one or more physical interactions (e.g., attractive or repulsive in nature) when two beads occupy neighboring sites (e.g., as determined by the interactions component 302). Thus, varying contributions to the one or more qubit Hamiltonians can be the set of configuration qubits (e.g., represented herein by "$q_{cf}$") of the first qubit registry and set of interaction qubits (e.g., represented herein by "$q_{in}$") of the second qubit registry. For example, the one or more qubit Hamiltonians can be characterized by Equation 17 below.

$$H(q) = H_{gc}(q_{cf}) + H_{lo}(q_{cf}) + H_{in}(q) + H_{ch}(q_{cf}) \quad (17)$$

Wherein "$H_{gc}$" can represent a growth constraint regarding a geometrical constraint that can govern the growths of the primary monomer sequence without bifurcation; "$H_{lo}$" can represent a local interactions constraint, wherein a local overlap that can penalize overlapping sequences; "$H_{in}$" can represent an interaction Hamiltonian regarding long range interactions between the monomers; and/or "$H_{ch}$" can represent a chirality constraint that can enforce the correct stereochemistry of the side chains.

For example, the energy level component 502 can determine the energy contributions for nearest neighbor interactions. For each pair of beads (i, j) the energy level component 502 can add an energy contribution of $\in_{i,j}^{(l)}$ to $H_{in}^{i,j}$ when the distance d(i,j)=l. However, a contribution of the form $\in_{i,j}^{(l)} \delta(d(i,j)-l)$ may not be efficiently implemented as a qubit string Hamiltonian (e.g., wherein "$\delta(.)$" can stand for the Dirac delta function). Thus, the energy level component 502 can use the set of interaction qubits $q_{i,j}^l$ to define an energy term of the form $q_{i,j}^l(\in_{i,j}^{(l)} + \lambda(d(i,j)-l))$ for each value of l and $\lambda >> \in_{i,j}^{(l)}$. Thereby, the energy level component 502 can assign energy stabilization when the interaction qubit $q_{i,j}^l=1$ and d(i,j)=l simultaneously. If both constraints are not satisfied, the energy level component 502 can add a large positive energy contribution via the factor $\lambda$ that can overcome $\in_{i,j}^{(l)}$. In one or more embodiments, the energy level component 502 can prevent the simultaneous occupation of a single lattice points by two beads. For example, the energy level component 502 can prevent overlaps that can occur in the vicinity of an interacting pair of monomers. If $q_{i,j}^l=1$, the energy level component 502 can apply one or more penalty functions so that i and j+1 cannot overlap when l=1, for instance.

In one or more embodiments, the energy level component 502 can express the condition that two turns are the same where T(i, j) returns 1 if $t_i$ and $t_j$ encode for the same axis (e.g., $t_i$ and $t_j$ encode the same axis but different directions) in accordance with Equation 18 below.

$$T(i,j) = \Sigma_{\alpha=\{0,1,2,3\}} f_\alpha(i) f_\alpha(j) \quad (18)$$

Further, in accordance with a sparse encoding scheme, the energy level component 502 can impose that one of the qubits that define a turn (e.g., four qubits in a tetrahedral lattice) is equal to one. Thereby, part of the qubit Hamiltonian can be omitted if the input state is such that there is one particle for every four qubits; thus, the qubit Hamiltonian can be explicated in accordance with Equation 19 below, wherein "$\lambda$" can be a large positive value.

$$H_{optional} = \Sigma_{i=3}^{N-1} \lambda (q_{4i-3} + q_{4i-2} + q_{4i-1} + q_{4i} - 1)^2 \quad (19)$$

In addition, the energy level component 502 can eliminate potential monomer sequence structures in which the same axis is chosen two or more times in a row. Thereby, the energy level component 502 can promote the generation of qubit Hamiltonians that can facilitate the determinations of multiple possible heteropolymer structures while avoiding repeating monomer sequence structures. For example, the energy level component 502 can define the Hamiltonian growth constant so as to apply one or more penalties (e.g., represented by $\lambda_{back}$ if two consecutive pairs of qubits encoding the turns of the heteropolymer's backbone are the same, in accordance with Equation 20 below.

$$H_{gc} = \Sigma_{i=3}^{N-1} \lambda_{back} T(i,j+1) \quad (20)$$

Wherein the energy level component 502 can control the number of 2-local terms appearing in the sum. Also, for a degree of branching by the heteropolymer structure that is defined by s>1, the energy level component 502 can add terms to avoid turnarounds inside one or more side chain structures.

Further, the energy level component 502 can define the Hamiltonian local interactions constraint so as to differentiate the interactions between beads that are near each other in the given structure sequence and possible interactions between beads that are further apart in an unfolded conformation. For example, in defining the local interactions constraint, the energy level component 502 can ignore interactions between beads that are first and second nearest neighbors in the primary sequence (e.g., the backbone sequence) as they can be the same in multiple conformations of the given heteropolymer. Wherein a tetrahedral lattice is utilized, the lattice can also inhibit two beads being linked by 3 or 4 beads to interact. Therefore, the energy level component 502 can introduce the local interactions component to treat interactions between beads that are linked by a sufficient number of beads (e.g., at least 5 bonds where the lattice has a tetrahedral geometry) but do not belong to monomers that are at a threshold distance in the primary sequence (e.g., a threshold distance of 4 beads where the lattice has a tetrahedral geometry).

For instance, in an exemplary heteropolymer structure comprising 1 side chain bead per monomer and developed on a tetrahedral lattice, the energy level component 502 can consider interactions between beads $i^{(1)}$ and $(i+3)^{(1)}$ at least because the beads can be linked by 5 bonds while belonging to monomers i and i+3. The energy level component 502 can express the condition wherein $i^{(1)}$ and $(i+3)^{(1)}$ are nearest neighbors on the lattice as equal to 1 when the condition is fulfilled in accordance with Equation 21 below.

$$C_{i^{(1)},(i+3)^{(1)}} = T(i^{(1)}, i+2)T(i,(i+3)^{(1)}) \quad (21)$$

For example, the energy level component 502 can consider an exemplary set of turns (e.g., $t_k t_{k+1} t_{k+2} t_{k+3} t_{k+4}$) linking two beads that are 5 bonds apart on a tetrahedral lattice and can provide a Hamiltonian constraint "$H_{back}$", wherein the distance between the beads can be 1 if $(t_k=t_{k+3}) \cap (t_{k+1}=t_{k+4})$. For instance, the Hamiltonian local interactions constrain can be defined by the energy level component 502 in accordance with Equation 22 below.

$$H_{lo} = \sum_{i=1}^{N-3} C_{i^{(1)},(i+3)^{(1)}} \epsilon_{i^{(1)},(i+3)^{(1)}} \quad (22)$$

Wherein additional beads are considered for side chains (e.g., wherein s≥2), additional terms can be added as well as one or more penalty functions (e.g., the number of terms in $H_{lo}$ can evolve linearly with N).

Additionally, the energy level component 502 can define one or more Hamiltonian chirality constraints, wherein the position of a first bead $i^{(1)}$ on the side chain of bead i can be imposed by the choice of the turn $t_{i-1}$, $t_i$, and, for example, the chirality of the monomer in the heteropolymer. Further, the growth of the side chains can be encoded to the first qubit registry (e.g., via the configuration component 114). The energy level component 502 can add the one or more chirality constraints to facilitate chirality. For example, consider the expected expression of $f_a^{ex}(i^{(1)})$ in terms of $f_a(i-1)$ and $f_a(i)$ defined in Equation 7. By analyzing multiple cases, the energy level component 502 can generate Table 1 and 2 below, which can contain information to express $f_a(i^{(1)})$ for $a \in \{0,1,2,3\}$.

TABLE 1

|  | $t_i$ | | | |
|---|---|---|---|---|
| $t_{i-1}$ | 0 | 1 | 2 | 3 |
| $\bar{0}$ |  | 2 | 3 | 1 |
| $\bar{1}$ | 3 |  | 0 | 2 |
| $\bar{2}$ | 1 | 3 |  | 0 |
| $\bar{3}$ | 2 | 0 | 1 |  |

TABLE 2

|  | $t_i$ | | | |
|---|---|---|---|---|
| $t_{i-1}$ | $\bar{0}$ | $\bar{1}$ | $\bar{2}$ | $\bar{3}$ |
| 0 |  | $\bar{3}$ | $\bar{1}$ | $\bar{2}$ |
| 1 | $\bar{2}$ |  | $\bar{3}$ | $\bar{0}$ |

TABLE 2-continued

|  | $t_i$ | | | |
|---|---|---|---|---|
| $t_{i-1}$ | $\bar{0}$ | $\bar{1}$ | $\bar{2}$ | $\bar{3}$ |
| 2 | $\bar{3}$ | $\bar{0}$ |  | $\bar{1}$ |
| 3 | $\bar{1}$ | $\bar{2}$ | $\bar{0}$ |  |

Additionally, the energy level component 502 can introduce an indicator for the parity (e.g., represented by "$g_i$"), which can be zero if I is even and one otherwise and can be defined as $$g_i = \frac{1-(-1)^i}{2}.$$

Based on Table 1 and parity indicator, the energy level component 502 can determine the $f_a^{ex}(i^{(1)})$ in accordance with Equations 23-30 below.

$$f_0^{ex}(i^{(1)}) = (1-g_i)(f_1(i-1)f_2(i)+f_2(i-1)f_3(i)+f_3(i-1)f_1(i)) \quad (23)$$

$$+g_i(f_1(i)f_2(i-1)+f_2(i)f_3(i-1)+f_3(i)f_1(i-1)) \quad (24)$$

$$f_1^{ex}(i^{(1)}) = (1-g_i)(f_0(i-1)f_3(i)+f_2(i-1)f_0(i)+f_3(i-1)f_2(i)) \quad (25)$$

$$+g_i(f_0(i)f_3(i-1)+f_2(i)f_0(i-1)+f_3(i)f_2(i-1)) \quad (26)$$

$$f_2^{ex}(i^{(1)}) = (1-g_i)(f_0(i-1)f_1(i)+f_1(i-1)f_3(i)+f_3(i-1)f_0(i)) \quad (27)$$

$$+g_i(f_0(i)f_1(i-1)+f_1(i)f_3(i-1)+f_3(i)f_0(i-1)) \quad (28)$$

$$f_3^{ex}(i^{(1)}) = (1-g_i)(f_0(i-1)f_2(i)+f_1(i-1)f_0(i)+f_2(i-1)f_1(i)) \quad (29)$$

$$+g_i(f_0(i)f_2(i-1)+f_1(i)f_0(i-1)+f_2(i)f_1(i-1)) \quad (30)$$

Thereby, the energy level component 502 can add the chirality constraint to enforce the chirality of the heteropolymer. The energy level component 502 can determine the axis to be chosen based on the expected values $f_a^{ex}(i^{(1)})$. For example, if the expected value equals one, the energy level component 502 can add a penalty (e.g., "$\lambda_{chirality}$") if $f_a(i^{(1)}) = 0$ in accordance with Equation 31 below.

$$H_{ch} = \lambda_{chirality} \Sigma_a \Sigma_{i=2}^{N-1} (1-f_a(i^{(1)})) 0 f_a^{ex}(i^{(1)}) \quad (31)$$

Furthermore, the energy level component 502 can define the interactions Hamiltonian based on various Hamiltonians (e.g., represented by "$H^{(l)}$") corresponding to the $l^{th}$ nearest neighbor interactions, for example, in accordance with Equation 32 below.

$$H_{in} = H^{(1)} + H^{(2)} + H^{(3)} + \quad (32)$$

For example, a relatively low number of terms in the interactions Hamiltonian can be achieved by utilizing a tetrahedral lattice. For instance, two beads (e.g., j and i with j≥i+4) can indifferently represent backbone beads or side chain beads such that the absolute distance in bonds can be analyzed (e.g., $j^{(1)} - i \equiv j-i+1$ or $j^{(1)} - i^{(1)} \equiv j-i+2$). The energy level component 502 can observe that the parity of j−i can be the parity of d(i, j). Further, the energy level component 502 can choose at least one more time along the positive direction if the monomer sequence begins by an even turn in accordance with Equation 33 below.

$$(j-i) = \begin{cases} 0 \mod 2 \text{ then } \sum_a \Delta n_a(i,j) = 0 \\ 1 \mod 2 \text{ then } \sum_a \Delta n_a(i,j) = (-1)^i \end{cases} \quad (33)$$

Wherein the energy level component 502 can introduce a notation for nearest neighbors of bead i, which can be denoted as "$\mathcal{N}$ (i)". For example, $\mathcal{N}$ (i)={i−1, i+1, i$^{(1)}$} if i is not at the end of the heteropolymer or $\mathcal{N}$ (i$^{(1)}$)={i} when limited to one side chain bead per monomer. Also, the interactions qubits can be qubits comporting two indices: $q_{ij}^{(l)}$, $q_{i^{(1)}j}^{(l)}$, $q_{ij^{(1)}}^{(l)}$, $q_{i^{(1)}j^{(1)}}^{(l)}$, for example.

Regarding first nearest neighbor interactions (e.g., represented by "H$^{(1)}$"), $q_{ij}^{(1)}$ can describe a contact between beads i and j that can belong to different lattice points and that can be any far apart bead. If the contact occurs, the interactions Hamiltonian can account for the contact energy $\epsilon_{ij}^{(1)}$ such that the first term can be $q_{ij}^{(1)}\epsilon_{ij}^{(1)}$. The condition for the gain in energy can be that the two subject beads see each other at a distance equal to one. Therefore, the energy level component 502 can add a constraint, wherein $q_{ij}^{(l)}=1$ the constraint can be denoted as $q_{ij}^{(1)}\lambda_1(d(i,j)-1)$.

Moreover, if $r \in \mathcal{N}$ (j) and i and j are first nearest neighbors, r can either overlap with i or be at a distance of 2 from i. The energy level component 502 can enforce the second case in order to account for the contact energy of i and j. The constraint can be defined as $q_{ij}^{(1)}\lambda_2(2-d(i,j)-1)$ with $\lambda_2$ being a large positive value; which can thereby inhibit a local overlap of the structure near the native contact. Thus, first nearest neighbor interactions can be determined in accordance with Equation 34 and 35 below.

$$H^{(1)} = \sum_{i=1}^{N-4} \sum_{\substack{j \geq i+5 \\ j-i=1 \mod 2}}^{N} h_{i,j}^{(1)} \quad (34)$$

With $$h_{ij}^{(1)} = \quad (35)$$

$$q_{ij}^{(1)}\left(\epsilon_{ij}^{(1)} + \lambda_1(d(i,j)-1) + \sum_{r \in \mathcal{N}(j)} \lambda_2(2-d(i,r)) + \sum_{m \in \mathcal{N}(i)} \lambda_2(2-d(m,j))\right)$$

Wherein the energy level component 502 can encourage the term in the parentheses to be positive in the general case where i and j are not in contact. For example, the energy level component 502 can control $\mathcal{N}$ (i)|≤3 and −(j−i+1)<d(i,r)−d(i,j)<(j−i+1) when $r \in \mathcal{N}$ (j), such that $\lambda_1 > 6(j-i+1)\lambda_2 + \epsilon_{ij}^{(1)}$, wherein the penalty values can depend on i and j.

In addition, the energy level component 502 can analyze the second nearest neighbor interactions between i and j that are on the same sublattice by introducing one or more new interaction qubits (e.g., represented by "$q_{ij}^{(2)}$"). For example, there can be multiple possible configurations that can lead to a second nearest neighbor interaction, wherein multiple interaction qubits can be utilized for the pair (i,j). The energy level component 502 can account for the various possibilities by splitting the Hamiltonian in accordance with Equation 36 below.

$$H^{(2)} = H^{(2)}[1] + H^{(2)}[3,3] + H^{(2)}[3,5] + H^{(2)}[5,3] \quad (36)$$

Further, one or more of the configurations can lead to a contact between r and i or m and i where (r, m) ∈ $\mathcal{N}$ (j), and can be accounted for by "H$^{(2)}$[1]" in accordance with Equations 37 and 38 below.

$$H^{(2)}[1] = \sum_{i=4}^{N-4} \sum_{\substack{j \geq i+4 \\ j-i=0 \mod 2}}^{N} h_{ij}^{(2)}[1] \quad (37)$$

Where $$h_{ij}^{(2)} = \sum_{r \in \mathcal{N}(j)} q_{i,r}^{(1)} \epsilon_{i,j}^{(2)} \quad (38)$$

In the following (r, m) ∈ $\mathcal{N}$ (j), the remaining configurations can be identified by different pair of distances:
 [3,3]: d(i, r)=3 and d(i, m)=3
 [3,5]: d(i, r)=3 and d(i, m)=5
 [5,3]: d(i, r)=5 and d(i, m)=3
Thus, the energy level component 502 can introduce three second contact qubits $q_{ij}^{(2)}[3,3]$, $q_{ij}^{(2)}[3,5]$, $q_{ij}^{(2)}[5,3]$, and build a Hamiltonian, for instance, in accordance with Equation 39 below.

$$H^{(2)}[3,5] = \sum_{i=1}^{N-4} \sum_{\substack{j \geq i+4 \\ j-i=0 \mod 2}}^{N} h_{ij}^{(2)}[3,5] \quad (39)$$

with $$h_{ij}^{(2)}[3,5] = (1-q_{i,r}^{(1)})(1-q_{i,m}^{(1)})q_{ij}^{(2)}[3,5]$$

$$\left(\epsilon_{ij}^{(2)} + \lambda_2(d(i,j)-2) + \lambda_3(3-d(i,r)) + \lambda_5(5-d(i,m))\right)$$

In various embodiments, the energy level component 502 can check that $q_{i,r}^{(1)} \neq 1$ and $q_{i,m}^{(1)} \neq 1$ so as not to count twice the interactions energy $\epsilon_{i,j}^{(2)}$. For example, the energy level component 502 can choose $\lambda_2, \lambda_3, \lambda_5$ such that the term in the parenthesis can be positive if d(i, j)≠ 2. Thereby, the energy level component 502 can adopt orientation-dependent l$^{th}$ nearest neighbor interaction energies for l>1. The number of qubits utilized can evolve exponentially with l that can define the accuracy of the course-grain model.

Figure 7:
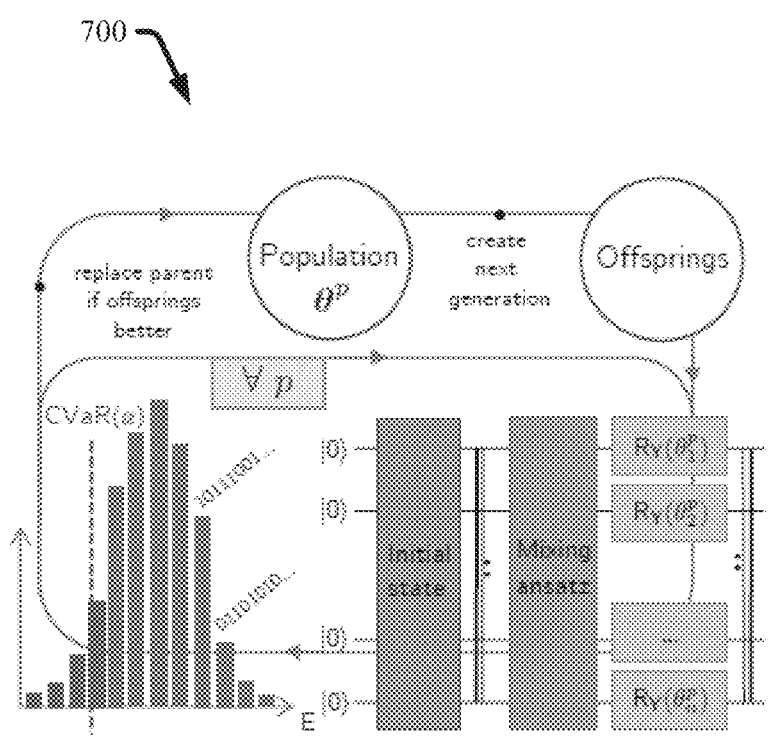
FIG. 7 illustrates a diagram of an example, non-limiting flow process that can depict one or more functions of a system that can generate one or more course-grain lattice models to determine the three-dimensional structure of a heteropolymer in accordance with one or more embodiments described herein.

FIG. 7 illustrates a diagram of the example, non-limiting system 100 further comprising optimization component 602 in accordance with one or more embodiments described herein. Repetitive description of like elements employed in other embodiments described herein is omitted for sake of brevity. In various embodiments, the optimization component 602 can analyze one or more wavefunctions generated by a quantum circuit (e.g., comprised within the one or more quantum computers 108) that includes the first and/or second qubit registries, wherein the wavefunctions can correspond to a plurality of conformations describing the three-dimensional structure of the heteropolymer. Further, the optimization component 602 can determine an optimal conformation from the plurality of conformations based on the wavefunctions and/or the energy of conformations.

For example, the optimal configuration describing the three-dimensional structure of the heteropolymer can correspond to the ground state of the Hamiltonian ("H(q)") generated by the energy level component 502 and can lie in the $2^{N_{cf}}$ dimensional space of the configuration qubits. The optimization component 602 can utilize one or more variational quantum circuits of the one or more quantum computers 108 comprising the first and/or second qubit registries (e.g., the configuration qubits and/or the interactions qubits). In one or more embodiments, the variational quantum circuit can comprise an initialization block with Hadamard and/or parametrized single qubit (e.g., $R_y$) gates followed by an entangling block and/or another set of single qubit rotations.

The optimization component 602 can denote a set of angles (e.g., $\theta=(\theta^{cf}, \theta^{in})$) of size 2n where "n" can represent the total number of qubits (e.g., defined as $n=N_{cf}+N_{ct}$), wherein $N_{cf}$ can represent the number configuration qubits and/or $N_{ct}$ can represent the number of interaction qubits.

Further, the optimization component 602 can optimize the angles (e.g., represented by "$\theta$") using a modified version of the Variational Quantum Eigensolver ("VQE") algorisms, referred to herein as conditional value-at-risk ("CVaR") VQE ("CVaR-VQE") algorithms. For example, the CVaR-VQE algorithm can define an objective function based on the average over the tail of a distribution delimited by a value (e.g., represented by "$\alpha$"). The optimization component 602 can define the CVaR-VQE algorithm in accordance with Equation 40 below.

$$\text{CVaR}_\alpha(\theta) = \langle \psi(\theta)|H(q)|\psi(\theta)\rangle_\alpha \qquad (40)$$

The optimization component 602 can optimize the gate parameters performed using a differential evolution ("DE") evolutionary optimizer that can mimic natural selection in the space of the angles (e.g., represented by "$\theta$").

In various embodiments, the optimization component 602 can define the scaling of the $\text{CVaR}_\alpha$ algorithm as the number of terms (e.g., Pauli strings), in the n-qubit Hamiltonian H(q) in accordance with Equation 41 below.

$$H(q) = \sum_\gamma^{N_t} h_\gamma \bigotimes_{i=1}^n q_i^{\gamma_i} \qquad (41)$$

Wherein "$h_\gamma$" can represent real coefficients. Additionally, $q_i=(1-\sigma_i^z)/2$ where $\sigma_i^z$ is Z Pauli matrix with $\gamma_i \in \{0,1\}$, and $N_t$ can be the total number of terms.

For instance, the geometrical constraints imposed by a tetrahedral lattice can give rise to possible 2-local terms within the $N_{cf}$ conformation qubits. Due to the entanglement with interaction qubits, the Hamiltonian locality (e.g., the maximum number of Pauli operators different from the identity in H(q)) can be a value of 3 for nearest neighbor interactions. Moreover, the scaling can be bound by $$N_t \sim N_{in} \binom{N_{cf}}{2} = O(N^4)$$

even for $l^{th}$ nearest neighbor interactions, with $l \geq 1$.

FIG. 7 illustrates a diagram of an example, non-limiting optimization process 700 that can be performed by the polymer folding component 110 (e.g., via optimization component 602) in accordance with one or more embodiments described herein. Repetitive description of like elements employed in other embodiments described herein is omitted for sake of brevity.

As shown in FIG. 7, one or more variational quantum circuits can generate multiple possible conformations describing the three-dimensional structures of the heteropolymer in accordance with the various functions of the polymer folding component 110 described herein (e.g., configuration component 114 and/or interactions component 302). Thereby, the one or more variational quantum circuits can generate a population of parent configurations delineated, for example, by the histogram shown in FIG. 7. The optimization component 502 can subject each configuration parent (e.g., represented by "$\theta^{pn}$") to a parametrized recombination with other configurations of the population to generate one or more offspring conformations. For example, the optimization component 602 can analyze the trail wavefunctions generated by the one or more variational quantum circuits to evaluate the $\text{CVaR}_\alpha$ objective function. Further, parent conformations and offspring conformations can be compared to update the configuration population at the next generations by the variational quantum circuit.

Throughout the optimization process 700 the wavefunctions $|\psi(\theta^p)\rangle$ corresponding to the different individual $\theta^p$ can be collapsed by the optimization component 602 during measurement leading to binary strings, which can be uniquely mapped to corresponding configurations and/or energies. Further, the optimization component 602 can denote by $\mathbb{P}_f(p)$ the probability for the individual configuration p to find the $f^{th}$ lowest energy fold at convergence.

Figure 8:
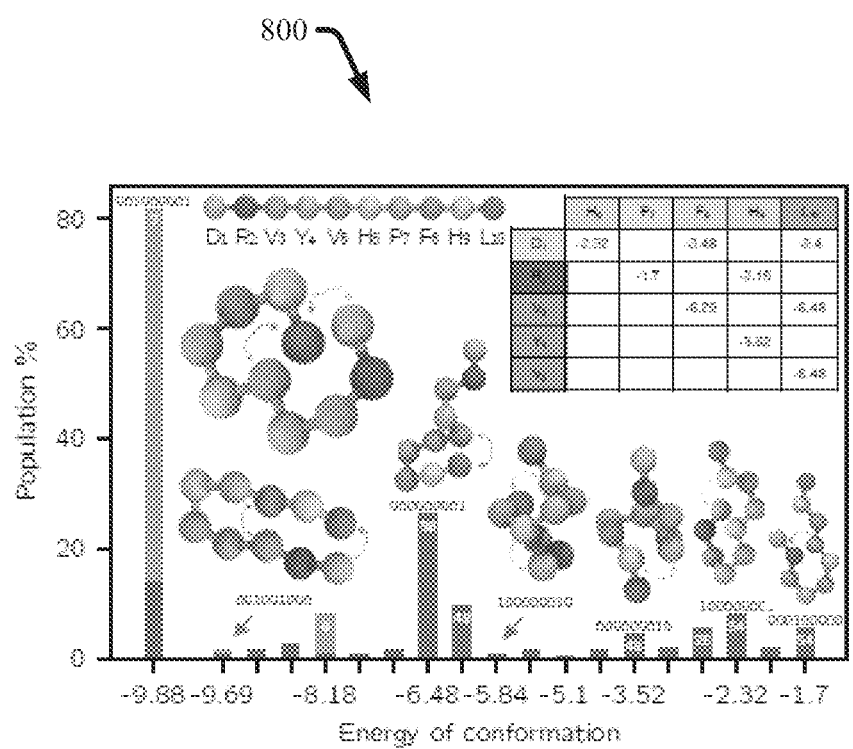
FIG. 8 illustrates a diagram of an example, non-limiting graph that can depict various folding conformations that can characterize the three-dimensional structure of a heteropolymer in accordance with one or more embodiments described herein.

FIG. 8 illustrates a diagram of an example, non-limiting energy graph 800 that can be generated by the polymer folding component 110 in accordance with one or more embodiments described herein. Repetitive description of like elements employed in other embodiments described herein is omitted for sake of brevity. In various embodiments, the energy level component 502 and/or the optimization component 602 can generate one or more graphs that can depict the energy of one or more configurations that can be encoded by the configuration component 114 and/or interactions component 302, such as the exemplary energy graph 800.

As shown in FIG. 8, the one or more graphs generated by the polymer folding component 110 (e.g., via the energy level component 502 and/or optimization component 602) can depict a monomer sequence of the given heteropolymer. For instance, exemplary energy graph 800 depicts the monomer sequence for the protein Angiotensin comprising the 10 amino acids: aspartic-acid (e.g., represented by "D"), Arginine (e.g., represented by "R"), valine (e.g., represented by "V"), tyrosine (e.g., represented by "Y"), histidine (e.g., represented by "H"), proline (e.g., represented by "P"), phenylalanine (e.g., represented by "F"), and/or leucine (e.g., represented by "L"). Additionally, the one or more graphs can depict the energy distribution at convergence of the low-energy fold obtained from the optimization component 602 via the CVaR-VQE algorithm and/or the DE optimizer. Further, binary strings can be associated with one or more configurations (e.g., represented by bars in the exemplary energy graph 800) can represent one or more interaction qubits defining the conformation's energy.

As depicted in exemplary energy graph 800, the numbers labelling the bars can correspond to the degeneracy of the conformations. Additionally, each of the amino acids depicted in FIG. 8 can be represented by a different shading to delineate different physical properties. Furthermore, the one or more graphs generated by the polymer folding component 110 (e.g., via the optimization component 602) can include one or more primary sequence and pairwise interaction matrices. For instance, the exemplary energy graph 800 includes a primary sequence of Angiotensin and pairwise interaction matrix for Angiotensin in the upper right corner.

In various embodiments, the CVaR-VQE algorithm can reduce the number of measurements required to minimize a classical cost function. Further, the construction of specific mixing ansatz can speed-up the search in the configuration space. Additionally, the direct connection between qubits and physical properties (e.g., configuration and interactions) can enable a rationalization of initialization of the qubit states and their entanglement. The locality of the Hamiltonian combined to the favorable scaling of the qubit resources and of the circuit depth with the number of monomers, can render the course-grain model described herein applicable with universal quantum computers 108 (e.g., including noisy intermediate-scale quantum computers and/or other types of quantum computers 108).

In one or more embodiments, the polymer folding component 110 can determine the three-dimensional structure of one or more proteins (e.g., to solve one or more protein folding problems). For example, the system 100 can determine the three-dimensional structure of the 10 amino acids peptide Angiotensin to illustrate one or more of the various features described herein. For instance, the polymer folding component 110 can use a coarse-grained model on a tetrahedral lattice with 28 qubits (e.g., comprised within one or more quantum computers 108) to determine the three-dimensional structure. In one or more embodiments, the polymer folding component 110 can utilize a dense encoding scheme of the polymer configuration that can utilize two qubits per turn, thus reducing the total number of utilized qubits to 22. Thereby, the dense encoding scheme can generate 5-local terms (e.g., as compared to a generation of 3-local terms by a sparse encoding scheme utilizing 28 qubits) in the qubit Hamiltonian while keeping the total number of Pauli strings within an affordable range for small instances.

To further reduce the number of qubits, the polymer folding component 110 can also integrate the side chains with the corresponding bead along the primary sequence and/or neglect interactions where l>1. The polymer folding component 110 (e.g., via the optimization component 602) can generate one or more graphs, such as exemplary energy graph 800, wherein each bin of the histogram can count over the population the occurrences of $\mathbb{P}_f(p)>0$ for a minimum energy fold (e.g., wherein f=0) and the next 18 folds given $n_s$=128 and $n_s$=1024 measurements of the wavefunctions during minimization. For example, the exemplary energy graph 800 depicts 80% of the individual configurations in the final population can generate the minimal conformations after 80 generations, which can occur with a probability $\max_p \mathbb{P}_f(p)$=42.2%.

Further, the polymer folding component 110 can reduce the number of measurements to 128 operations of the experiment used to derive a statistical sample for the probability distribution, the system 100 can obtained a broad spectrum of low energy conformations, which can include the global minimum with lower probability. As shown in the exemplary energy graph 800, the low-energy conformations (e.g., comprising energies below 0), the polymer folding component 110 can identify the formation of an α-helix and a β-sheet. By tuning the interaction matrix, the polymer folding component 110 can foster the formation of secondary structural elements for analyzation.

In another example, the polymer folding component 110 can determine the three-dimensional structure of a 7 amino acids neuropeptide with the sequence alanine ("A")-proline ("P")-arginine ("R")-leucine ("L")-arginine ("R")-phenylalanine ("F")-tyrosine ("Y").

Figure 9A:
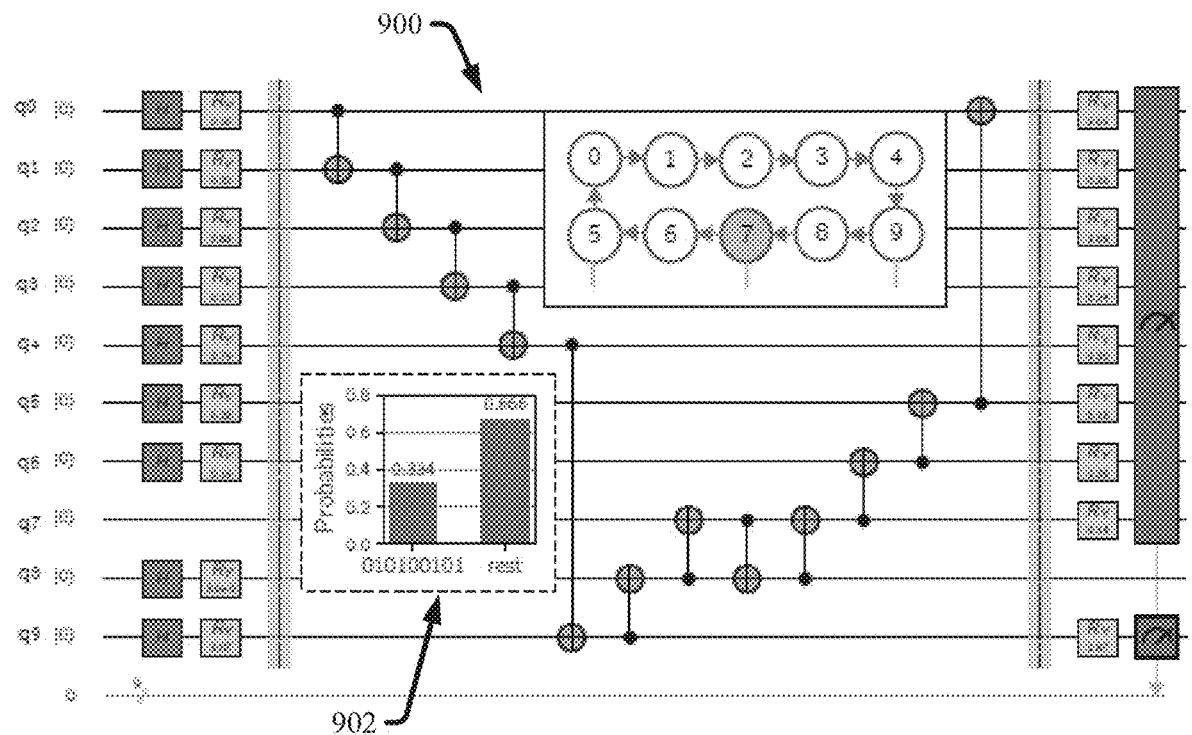
FIG. 9A illustrates a diagram of an example, non-limiting qubit registry that can encode one or more configurations of heteropolymer in accordance with one or more embodiments described herein.

FIG. 9A illustrates a diagram of an example, non-limiting parametrized quantum circuit 900 that can be encoded and/or analyzed by the polymer folding component 110 in accordance with one or more embodiments. Repetitive description of like elements employed in other embodiments described herein is omitted for sake of brevity. In one or more embodiments, the system 100 can determine the three-dimensional structure of a 7 amino acids neuropeptide with the sequence alanine ("A")-proline ("P")-arginine ("R")-leucine ("L")-arginine ("R")-phenylalanine ("F")-tyrosine ("Y") to further illustrate one or more of the various features described herein. The exemplary parametrized quantum circuit 900 shown in FIG. 9A can be encoded by the polymer folding component 110 to analyze the APRLRFY neuropeptide. As shown in FIG. 9A, the entangle block of the quantum circuit can comprise a closed-loop of CNOT gates that can fit the hardware connectivity of a 20 qubit quantum computer 108 (e.g., the 20-qubits IBM device Poughkeepsie). For example, qubit 7 can be used to close the loop by swapping with qubit 8, as shown in the exemplary parametrized quantum circuit 900. Additionally, graph 902 imposed on the exemplary parametrized quantum circuit 900 can depict the evolution of the CVaR energy function (e.g., α=5%) throughout a minimalization process by the optimization component 602.

Figure 9B:
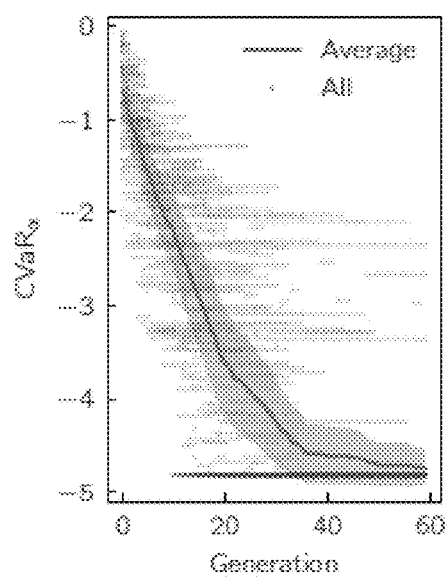
FIG. 9B illustrates a diagram of an example, non-limiting graph that can demonstrate the efficacy of a system that can autonomously determine one or more three-dimensional structures of one or more heteropolymers in accordance with one or more embodiments described herein.
Figure 9C:
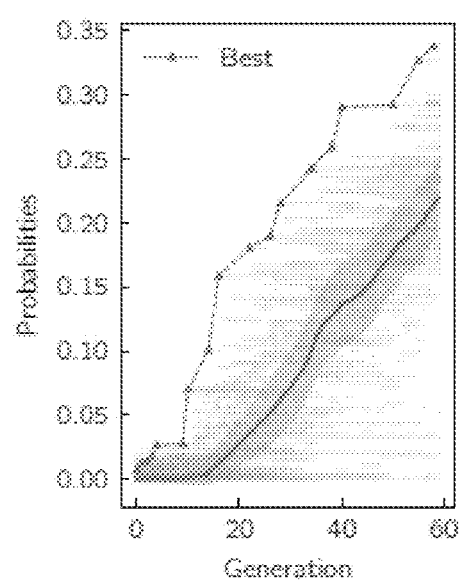
FIG. 9C illustrates a diagram of an example, non-limiting graph that can demonstrate the efficacy of a system that can autonomously determine one or more three-dimensional structures of one or more heteropolymers in accordance with one or more embodiments described herein.

FIGS. 9B and/or 9C illustrate example, non-limiting graphs that can depict the efficacy of the polymer folding component 110 determining the three-dimensional structure of the APRLRFY neuropeptide utilizing the exemplary parametrized quantum circuit 900 in accordance with one or more embodiments described herein. Repetitive description of like elements employed in other embodiments described herein is omitted for sake of brevity. For example, graph 904 can depict the mean $CVaR_\alpha$ energy value of the population as a function of the number of generations via robust and smooth convergence towards an optimal fold. Additionally, graph 906 can depict the average probability of the ground state averaged over the entire population, $\langle \mathbb{P}_0(p)\rangle$, wherein the average probability can increase monotonically to a final value larger than 20% and with $\max_p \mathbb{P}_0(p)$ peaking up at 33%.

Figure 10:
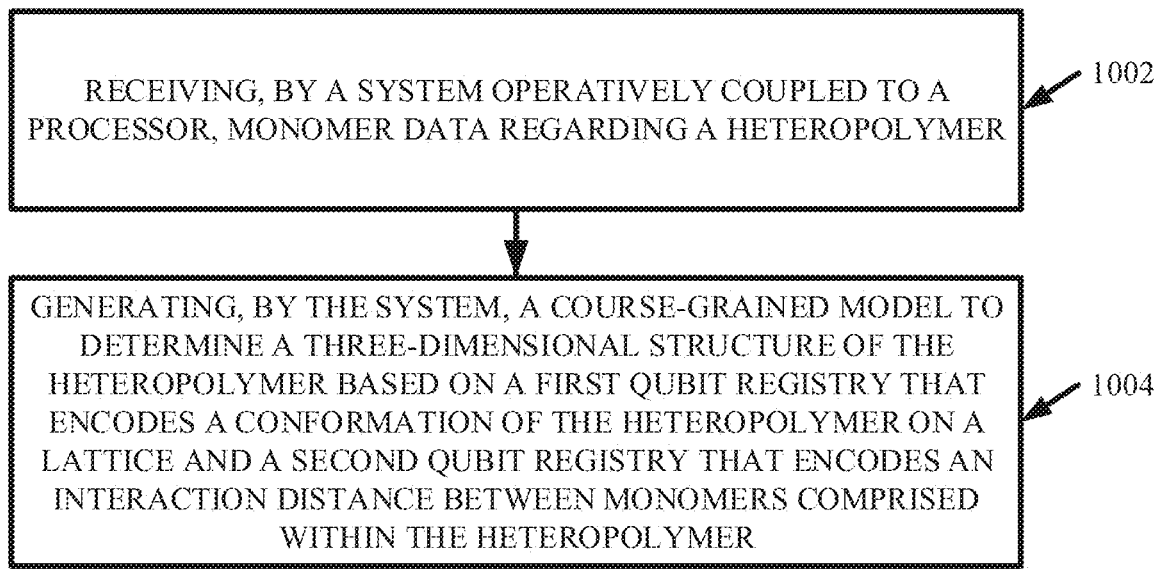
FIG. 10 illustrates a flow diagram of an example, non-limiting method that can facilitate generating one or more course-grain lattice models to determine the three-dimensional structure of a heteropolymer in accordance with one or more embodiments described herein.

FIG. 10 illustrates a flow diagram of an example, non-limiting method 1000 that determine one or more three-dimensional structures of one or more heteropolymers in accordance with one or more embodiments described herein. Repetitive description of like elements employed in other embodiments described herein is omitted for sake of brevity.

At 1002, the method 1000 can comprise receiving, by a system 100 (e.g., via the communications component 112) coupled to a processor 120, monomer data regarding one or more heteropolymers. The monomer data can regard one or more chemical and/or physical properties regarding a given heteropolymer. For example, the monomer data can delineate the type of monomers comprised within the heteropolymer along with one or more physical (e.g., size measurements) and/or chemical (e.g., interaction affinities) traits of the monomers. In various embodiments, one or more users of the system 100 can enter the monomer data via one or more input devices 106. Further, the monomer data can be stored in one or more memories 116.

At 1004, the method 1000 can comprise generating, by the system 100 (e.g., via configuration component 114, interactions component 302, energy level component 502, and/or optimization component 602), one or more course-grained models to determine the one or more three-dimensional structures of the one or more heteropolymers based on a first qubit registry that encodes one or more conformations of the one or more heteropolymers on a lattice and a second qubit registry that can encode one or more interaction distances between monomers comprised within the one or more heteropolymers. For example, the first and/or second qubit registries can be comprised within one or more variational quantum circuits of one or more quantum computers 108 (e.g., in accordance with one or more embodiments described herein, such as exemplary parametrized quantum circuit 900).

In various embodiments, the lattice can comprise one or more sets of lattice points associated with various possible direction in which the monomer sequence of the heteropolymer can develop. As the sequence of monomers develops from lattice point to lattice point along the possible directions, the method 1000 can comprise encoding (e.g., via configuration component 114) the development to the first qubit registry via a sequence of turns in relation to the lattice points. For example, the lattice can be a tetrahedral lattice comprising two non-equivalent and alternating sets of lattice points as depicted in FIGS. 2A and 2B. Further, the method 1000 can comprise encoding (e.g., via interactions component 302) the one or more interactions distances to the second qubit registry based on, for example, the encoded turn sequence and/or the lattice structure. For example, the one or more interactions distances can be encoded as one or more edges of the lattice as depicted by dashed lines in FIG. 4A. Based on the monomer data, encoded turn sequence, and/or encoded interaction distances, the method 1000 can further comprise defining (e.g., via energy level component 502) one or more qubit Hamiltonians to describe the energy of conformation of possible three-dimensional structures of the heteropolymer. Further, the method 1000 can comprise optimizing (e.g., via optimization component 602) the determination of possible three-dimensional structures (e.g., in accordance with the CVaR-VQE algorithm described herein) to prioritize low-energy conformations of the heteropolymer.

Figure 11:
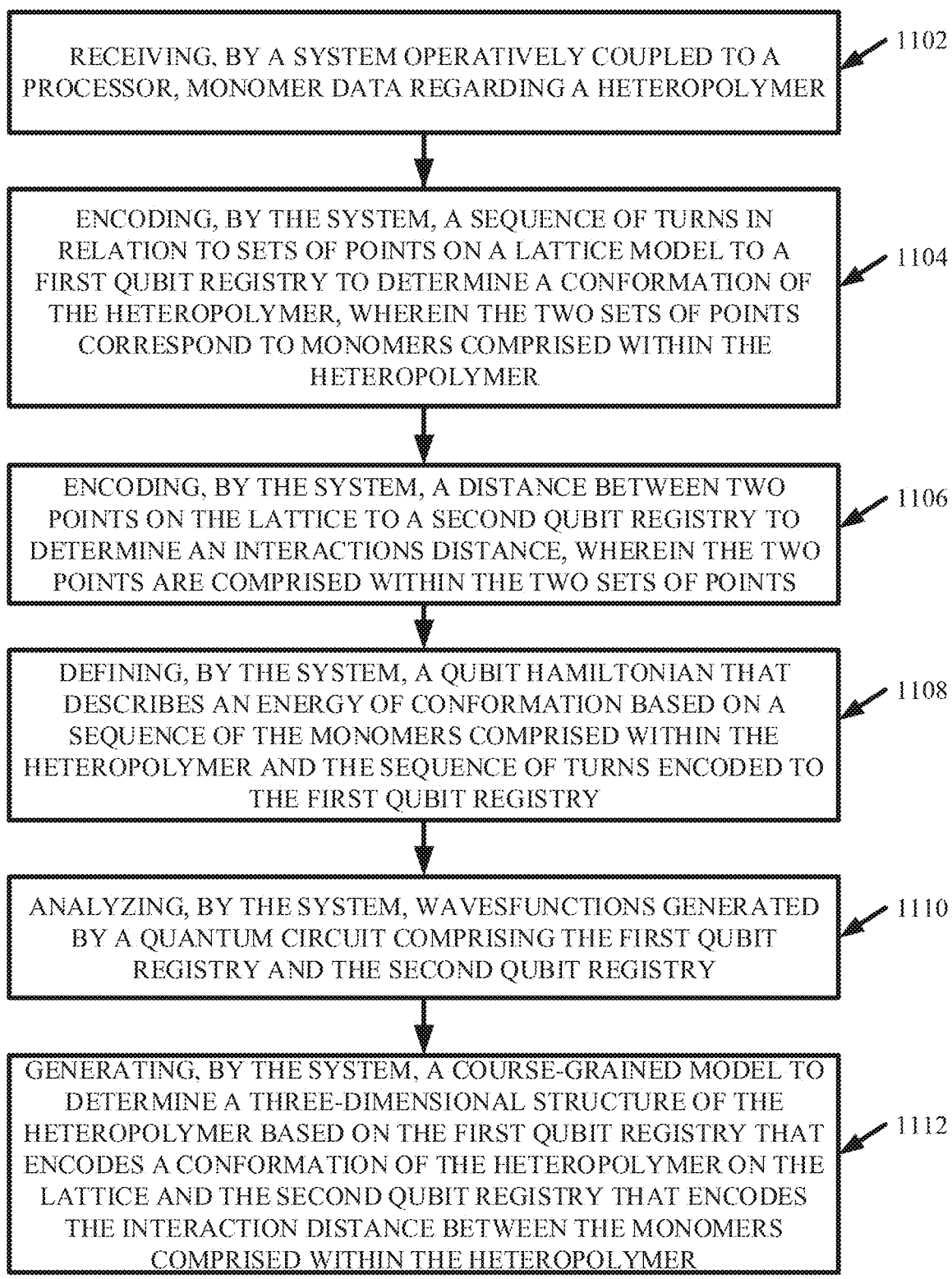
FIG. 11 illustrates a flow diagram of an example, non-limiting method that can facilitate generating one or more course-grain lattice models to determine the three-dimensional structure of a heteropolymer in accordance with one or more embodiments described herein.

FIG. 11 illustrates a flow diagram of an example, non-limiting method 1100 that determine one or more three-dimensional structures of one or more heteropolymers in accordance with one or more embodiments described herein. Repetitive description of like elements employed in other embodiments described herein is omitted for sake of brevity.

At 1102, the method 1100 can comprise receiving, by a system 100 (e.g., via the communications component 112) coupled to a processor 120, monomer data regarding one or more heteropolymers. The monomer data can regard one or more chemical and/or physical properties regarding a given heteropolymer. For example, the monomer data can delineate the type of monomers comprised within the heteropolymer along with one or more physical (e.g., size measurements) and/or chemical (e.g., interaction affinities) traits of the monomers. In various embodiments, one or more users of the system 100 can enter the monomer data via one or more input devices 106. Further, the monomer data can be stored in one or more memories 116.

At 1104, the method 1100 can comprise encoding, by the system 100 (e.g., via configuration component 114), a sequence of turns in relation to one or more sets of points on a lattice to a first qubit registry to determine one or more conformations of the one or more heteropolymers, wherein the two sets of points can correspond to monomers comprised within the one or more heteropolymers. For example, the lattice can comprise one or more sets of lattice points associated with various possible direction in which the monomer sequence of the heteropolymer can develop. For instance, the lattice can be a tetrahedral lattice comprising two non-equivalent and alternating sets of lattice points as depicted in FIGS. 2A and 2B.

At 1106, the method 1100 can comprise encoding, by the system 100 (e.g., via interactions component 302), one or more distances between two points on the lattice to a second qubit registry to determine one or more interactions distances, wherein the two points can be comprised within the two sets of points. For example, the one or more interactions distances can be encoded as one or more edges of the lattice as depicted by dashed lines in FIG. 4A. Further, the interaction distances can be based on the monomer sequence of the heteropolymer, the sequence of turns encoded to the first qubit, and/or the monomer data received at 1102.

At 1108, the method 1100 can comprise defining, by the system 100 (e.g., via energy level component 502), one or more qubit Hamiltonians that can describe one or more energy of conformations based on the sequence of monomers comprised within the heteropolymer and the sequence of turns encoded to the first qubit registry. For example, the one or more qubit Hamiltonians can be defined in accordance with Equation 17.

At 1110, the method 1100 can comprise analyzing, by the system (e.g., via optimization component 602), one or more wavefunctions generated by one or more quantum circuits comprising the first qubit registry and the second qubit registry. For example, the wavefunctions can be generated by one or more variational quantum circuits and/or analyzed via one or more CVaR-VQE algorithms and DE minimizations, for example, in accordance with exemplary optimization process 700.

At 1112, the method 1100 can comprise generating, by the system 100 (e.g., via the polymer folding component 114), one or more course-grained models to determine the three-dimensional structure of the heteropolymer based on the first qubit registry that can encode one or more conformations of the heteropolymer on the lattice and the second qubit registry that can encode the interactions distance between the monomers comprised within the heteropolymer. For example, the one or more course-grained models can include one or more graphs regarding one or more energies of conformations, such as exemplary energy graph 800.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 12:
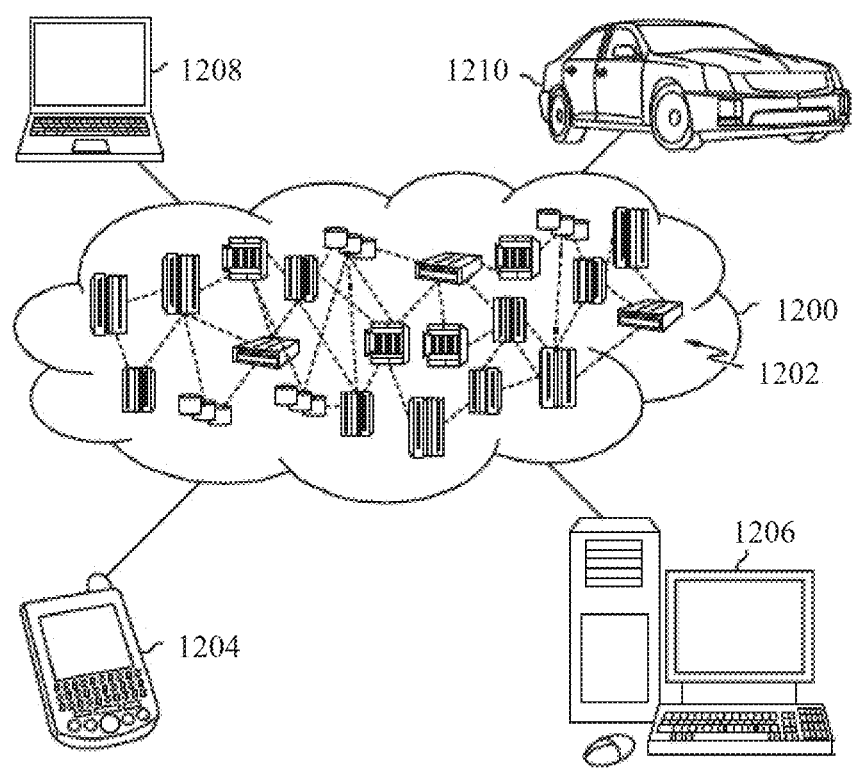
FIG. 12 depicts a cloud computing environment in accordance with one or more embodiments described herein.

Referring now to FIG. 12, illustrative cloud computing environment 1200 is depicted. As shown, cloud computing environment 1200 includes one or more cloud computing nodes 1202 with which local computing devices used by cloud consumers, such as, for example, personal digital assistant (PDA) or cellular telephone 1204, desktop computer 1206, laptop computer 1208, and/or automobile computer system 1210 may communicate. Nodes 1202 may communicate with one another. They may be grouped (not shown) physically or virtually, in one or more networks, such as Private, Community, Public, or Hybrid clouds as described hereinabove, or a combination thereof. This allows cloud computing environment 1200 to offer infrastructure, platforms and/or software as services for which a cloud consumer does not need to maintain resources on a local computing device. It is understood that the types of computing devices 1204-1210 shown in FIG. 12 are intended to be illustrative only and that computing nodes 1202 and cloud computing environment 1200 can communicate with any type of computerized device over any type of network and/or network addressable connection (e.g., using a web browser).

Figure 13:
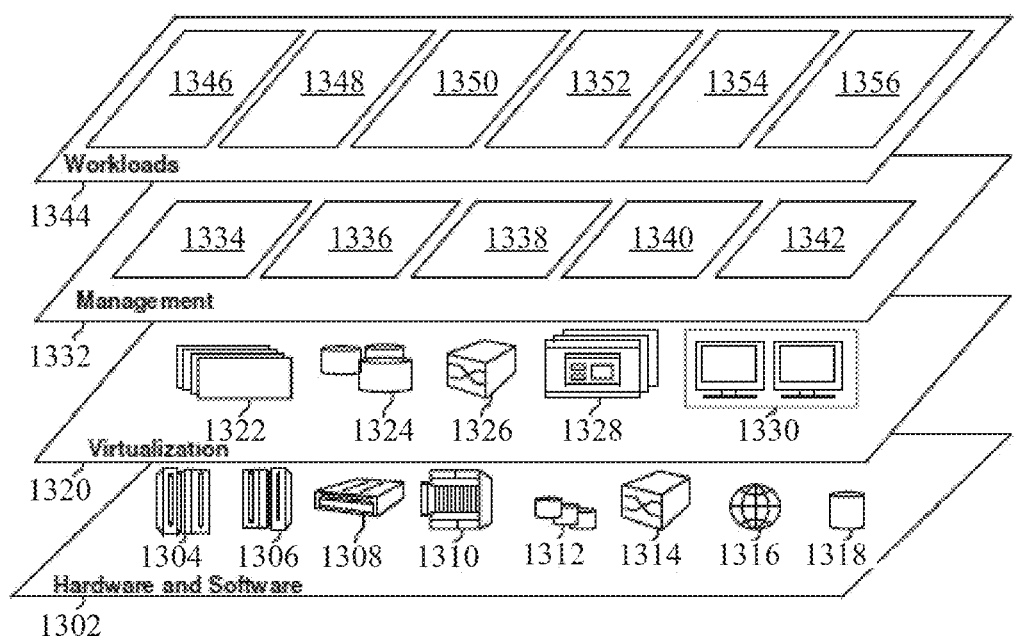
FIG. 13 depicts abstraction model layers in accordance with one or more embodiments described herein.

Referring now to FIG. 13, a set of functional abstraction layers provided by cloud computing environment 1200 (FIG. 12) is shown. Repetitive description of like elements employed in other embodiments described herein is omitted for sake of brevity. It should be understood in advance that the components, layers, and functions shown in FIG. 13 are intended to be illustrative only and embodiments of the invention are not limited thereto. As depicted, the following layers and corresponding functions are provided.

Hardware and software layer 1302 includes hardware and software components. Examples of hardware components include: mainframes 1304; RISC (Reduced Instruction Set Computer) architecture based servers 1306; servers 1308; blade servers 1310; storage devices 1312; and networks and networking components 1314. In some embodiments, software components include network application server software 1316 and database software 1318.

Virtualization layer 1320 provides an abstraction layer from which the following examples of virtual entities may be provided: virtual servers 1322; virtual storage 1324; virtual networks 1326, including virtual private networks; virtual applications and operating systems 1328; and virtual clients 1330.

In one example, management layer 1332 may provide the functions described below. Resource provisioning 1334 provides dynamic procurement of computing resources and other resources that are utilized to perform tasks within the cloud computing environment. Metering and Pricing 1336 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1338 provides access to the cloud computing environment for consumers and system administrators. Service level management 1340 provides cloud computing resource allocation and management such that required service levels are met. Service Level Agreement (SLA) planning and fulfillment 1342 provide pre-arrangement for, and procurement of, cloud computing resources for which a future requirement is anticipated in accordance with an SLA.

Workloads layer 1344 provides examples of functionality for which the cloud computing environment may be utilized. Examples of workloads and functions which may be provided from this layer include: mapping and navigation 1346; software development and lifecycle management 1348; virtual classroom education delivery 1350; data analytics processing 1352; transaction processing 1354; and heteropolymer structure processing 1356. Various embodiments of the present invention can utilize the cloud computing environment described with reference to FIGS. 12 and 13 to determine the three-dimensional structure of a heteropolymer.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

Figure 14:
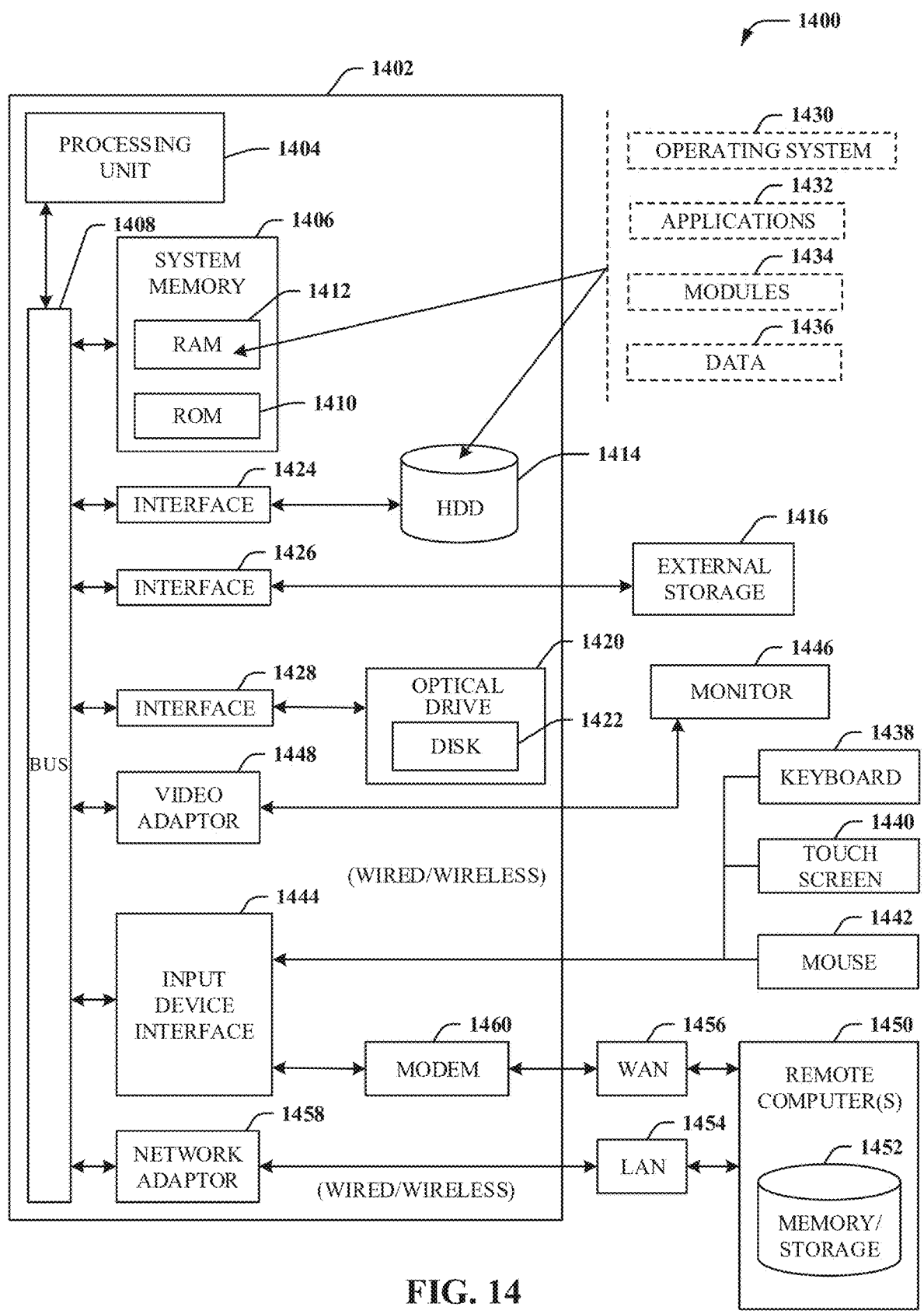
FIG. 14 illustrates a block diagram of an example, non-limiting operating environment in which one or more embodiments described herein can be facilitated.

In order to provide additional context for various embodiments described herein, FIG. 14 and the following discussion are intended to provide a general description of a suitable computing environment 1400 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things ("IoT") devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory ("RAM"), read only memory ("ROM"), electrically erasable programmable read only memory ("EEPROM"), flash memory or other memory technology, compact disk read only memory ("CD-ROM"), digital versatile disk ("DVD"), Blu-ray disc ("BD") or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 14, the example environment 1400 for implementing various embodiments of the aspects described herein includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures can also be employed as the processing unit 1404.

The system bus 1408 can be any of several types of bus structure that can further interconnect to a memory bus (with or without a memory controller), a peripheral bus, and a local bus using any of a variety of commercially available bus architectures. The system memory 1406 includes ROM 1410 and RAM 1412. A basic input/output system ("BIOS") can be stored in a non-volatile memory such as ROM, erasable programmable read only memory ("EPROM"), EEPROM, which BIOS contains the basic routines that help to transfer information between elements within the computer 1402, such as during startup. The RAM 1412 can also include a high-speed RAM such as static RAM for caching data.

The computer 1402 further includes an internal hard disk drive ("HDD") 1414 (e.g., EIDE, SATA), one or more external storage devices 1416 (e.g., a magnetic floppy disk drive ("FDD") 1416, a memory stick or flash drive reader, a memory card reader, etc.) and an optical disk drive 1420 (e.g., which can read or write from a CD-ROM disc, a DVD, a BD, etc.). While the internal HDD 1414 is illustrated as located within the computer 1402, the internal HDD 1414 can also be configured for external use in a suitable chassis (not shown). Additionally, while not shown in environment 1400, a solid state drive ("SSD") could be used in addition to, or in place of, an HDD 1414. The HDD 1414, external storage device(s) 1416 and optical disk drive 1420 can be connected to the system bus 1408 by an HDD interface 1424, an external storage interface 1426 and an optical drive interface 1428, respectively. The interface 1424 for external drive implementations can include at least one or both of Universal Serial Bus ("USB") and Institute of Electrical and Electronics Engineers ("IEEE") 1394 interface technologies. Other external drive connection technologies are within contemplation of the embodiments described herein.

The drives and their associated computer-readable storage media provide nonvolatile storage of data, data structures, computer-executable instructions, and so forth. For the computer 1402, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. The systems and methods described herein can be implemented utilizing various commercially available operating systems or combinations of operating systems.

Computer 1402 can optionally comprise emulation technologies. For example, a hypervisor (not shown) or other intermediary can emulate a hardware environment for operating system 1430, and the emulated hardware can optionally be different from the hardware illustrated in FIG. 14. In such an embodiment, operating system 1430 can comprise one virtual machine ("VM") of multiple VMs hosted at computer 1402. Furthermore, operating system 1430 can provide runtime environments, such as the Java runtime environment or the .NET framework, for applications 1432. Runtime environments are consistent execution environments that allow applications 1432 to run on any operating system that includes the runtime environment. Similarly, operating system 1430 can support containers, and applications 1432 can be in the form of containers, which are lightweight, standalone, executable packages of software that include, e.g., code, runtime, system tools, system libraries and settings for an application.

Further, computer 1402 can be enable with a security module, such as a trusted processing module ("TPM"). For instance with a TPM, boot components hash next in time boot components, and wait for a match of results to secured values, before loading a next boot component. This process can take place at any layer in the code execution stack of computer 1402, e.g., applied at the application execution level or at the operating system ("OS") kernel level, thereby enabling security at any level of code execution.

A user can enter commands and information into the computer 1402 through one or more wired/wireless input devices, e.g., a keyboard 1438, a touch screen 1440, and a pointing device, such as a mouse 1442. Other input devices (not shown) can include a microphone, an infrared ("IR") remote control, a radio frequency ("RF") remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1404 through an input device interface 1444 that can be coupled to the system bus 1408, but can be connected by other interfaces, such as a parallel port, an IEEE 1394 serial port, a game port, a USB port, an IR interface, a BLUETOOTH® interface, etc.

A monitor 1446 or other type of display device can be also connected to the system bus 1408 via an interface, such as a video adapter 1448. In addition to the monitor 1446, a computer typically includes other peripheral output devices (not shown), such as speakers, printers, etc.

The computer 1402 can operate in a networked environment using logical connections via wired and/or wireless communications to one or more remote computers, such as a remote computer(s) 1450. The remote computer(s) 1450 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1452 is illustrated. The logical connections depicted include wired/wireless connectivity to a local area network ("LAN") 1454 and/or larger networks, e.g., a wide area network ("WAN") 1456. Such LAN and WAN networking environments are commonplace in offices and companies, and facilitate enterprise-wide computer networks, such as intranets, all of which can connect to a global communications network, e.g., the Internet.

When used in a LAN networking environment, the computer 1402 can be connected to the local network 1454 through a wired and/or wireless communication network interface or adapter 1458. The adapter 1458 can facilitate wired or wireless communication to the LAN 1454, which can also include a wireless access point ("AP") disposed thereon for communicating with the adapter 1458 in a wireless mode.

When used in a WAN networking environment, the computer 1402 can include a modem 1460 or can be connected to a communications server on the WAN 1456 via other means for establishing communications over the WAN 1456, such as by way of the Internet. The modem 1460, which can be internal or external and a wired or wireless device, can be connected to the system bus 1408 via the input device interface 1444. In a networked environment, program modules depicted relative to the computer 1402 or portions thereof, can be stored in the remote memory/storage device 1452. It will be appreciated that the network connections shown are example and other means of establishing a communications link between the computers can be used.

When used in either a LAN or WAN networking environment, the computer 1402 can access cloud storage systems or other network-based storage systems in addition to, or in place of, external storage devices 1416 as described above. Generally, a connection between the computer 1402 and a cloud storage system can be established over a LAN 1454 or WAN 1456 e.g., by the adapter 1458 or modem 1460, respectively. Upon connecting the computer 1402 to an associated cloud storage system, the external storage interface 1426 can, with the aid of the adapter 1458 and/or modem 1460, manage storage provided by the cloud storage system as it would other types of external storage. For instance, the external storage interface 1426 can be configured to provide access to cloud storage sources as if those sources were physically connected to the computer 1402.

The computer 1402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity ("Wi-Fi") and BLUETOOTH® wireless technologies. Thus, the communication can be a predefined structure as with a conventional network or simply an ad hoc communication between at least two devices.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor, operably coupled to the memory, and that executes the computer executable components stored in the memory, wherein the computer executable components comprise:
      a polymer folding component that generates a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

2. The system of claim 1, wherein the first qubit registry and the second qubit registry are encoded on a universal quantum computer.

3. The system of claim 1, wherein the heteropolymer is a protein, and wherein the lattice has a tetrahedral geometry.

4. The system of claim 1, wherein the course-gained model is a two-centered model representing a backbone of the heteropolymer and a sidechain of the heteropolymer.

5. The system of claim 1, further comprising:
   a configuration component that encodes a sequence of turns in relation to two sets of points on the lattice to the first qubit registry to determine the conformation, wherein the two sets of points correspond to the monomers comprised within the heteropolymer.

6. The system of claim 5, wherein the two sets of points are alternating lattice points, wherein a first turn from the sequence of turns is in relation to a first set of points from the two sets of points, and wherein a second turn from the sequence of turns is in relation to a second set of points from the two sets of points.

7. The system of claim 5, further comprising:
   an interactions component that encodes a distance between two points on the lattice to the second qubit registry to determine the interaction distance, wherein the two points are comprised within the two sets of points.

8. The system of claim 7, further comprising:
   an energy level component that defines a qubit Hamiltonian that describes an energy of the conformation based on a sequence of the monomers comprised within the heteropolymer, the sequence of turns encoded to the first qubit registry, and the distance encoded to the second qubit registry.

9. The system of claim 8, further comprising:
   an optimization component that analyzes wavefunctions generated by a quantum circuit comprising the first qubit registry and the second qubit registry, wherein the wavefunctions correspond to a plurality of conformations describing the three-dimensional structure.

10. The system of claim 9, wherein the optimization component determines an optimal conformation from the plurality of conformations based on the wavefunctions and the energy of the conformation.

11. A computer-implemented method, comprising:
    generating, by a system operatively coupled to a processor, a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

12. The computer-implemented method of claim 11, further comprising:
    encoding, by the system, a sequence of turns in relation to two sets of points on the lattice to the first qubit registry to determine the conformation, wherein the two sets of points correspond to the monomers comprised within the heteropolymer.

13. The computer-implemented method of claim 12, further comprising:
    encoding, by the system, a distance between two points on the lattice to the second qubit registry to determine the interaction distance, wherein the two points are comprised within the two sets of points.

14. The computer-implemented method of claim 13, further comprising:
    defining, by the system, a qubit Hamiltonian that describes an energy of the conformation based on a sequence of the monomers comprised within the heteropolymer, the sequence of turns encoded to the first qubit registry, and the distance encoded to the second qubit registry.

15. The computer-implemented method of claim 14, further comprising:
    analyzing, by the system, wavefunctions generated by a quantum circuit comprising the first qubit registry and the second qubit registry to determine the three-dimensional structure based on the energy of the conformation.

16. A computer program product for determining a folding of a polymer chain, the computer program product comprising a non-transitory computer readable storage medium having program instructions embodied therewith, the program instructions executable by a processor to cause the processor to:
    generate, by the processor, a course-grained model to determine a three-dimensional structure of a heteropolymer based on a first qubit registry that encodes a conformation of the heteropolymer on a lattice and a second qubit registry that encodes an interaction distance between monomers comprised within the heteropolymer.

17. The computer program product of claim 16, wherein the program instructions further cause the processor to:
    encode, by the processor, a sequence of turns in relation to two sets of points on the lattice to the first qubit registry to determine the conformation, wherein the two sets of points correspond to the monomers comprised within the heteropolymer; and
    encode, by the processor, a distance between two points on the lattice to the second qubit registry to determine the interaction distance, wherein the two points are comprised within the two sets of points.

18. The computer program product of claim 17, wherein the program instructions further cause the processor to:
  define, by the processor, a qubit Hamiltonian that describes an energy of the conformation based on a sequence of the monomers comprised within the heteropolymer, the sequence of turns encoded to the first qubit registry, and the distance encoded to the second qubit registry.

19. The computer program product of claim 18, wherein the program instructions further cause the processor to:
  analyze, by the processor, wavefunctions generated by a quantum circuit comprising the first qubit registry and the second qubit registry to determine the three-dimensional structure based on the energy of the conformation.

20. The computer program product of claim 19, wherein the processor analyzes the wavefunctions via a cloud computing environment.

* * * * *